United States Patent [19]
Suzuki

[11] Patent Number: 5,817,138
[45] Date of Patent: Oct. 6, 1998

[54] MULTI-CHANNEL, INTERFERENTIAL WAVE, MICRO CURRENT DEVICE AND METHODS FOR TREATMENT USING MICRO CURRENT

[76] Inventor: James Y. Suzuki, 5766 S. Oaklawn Pl., Seattle, Wash. 98118

[21] Appl. No.: 758,637

[22] Filed: Nov. 27, 1996

[51] Int. Cl.$^6$ ........................................................ A61N 1/36
[52] U.S. Cl. .............................................................. 607/67
[58] Field of Search ................................. 607/66, 67, 68, 607/69, 70, 71, 72

[56] References Cited

U.S. PATENT DOCUMENTS

| | | | |
|---|---|---|---|
| 5,285,781 | 2/1994 | Brodard | 607/66 |
| 5,324,317 | 6/1994 | Reiss | 607/67 |

OTHER PUBLICATIONS

Cheng, et al. Arch. Dermatol. vol. 129, pp. 264–271 (1993).
Wood, et al. Arch. Dermatol. vol. 129, pp. 999–1008 (1993).

*Primary Examiner*—Scott M. Getzow
*Attorney, Agent, or Firm*—George W. Neuner

[57] ABSTRACT

An interferential wave, micro current device is disclosed. The device typically has a power supply, a frequency generator, a pulse generator, a pulse envelope generator, an electrical current controller, and four or more channels for applying micro amperes of electrical current to patient tissue. Each channel has two electrodes for completing a micro current electrical circuit through patient tissue. The controller provides a controlled amount of current in each channel from about 20 micro amperes to about 200 micro amperes at a frequency up to about 300 Hertz. Also disclosed are methods for treating lymphedema, edema, fibrosis and fibromylagea by application of interferential wave form micro current.

30 Claims, 28 Drawing Sheets

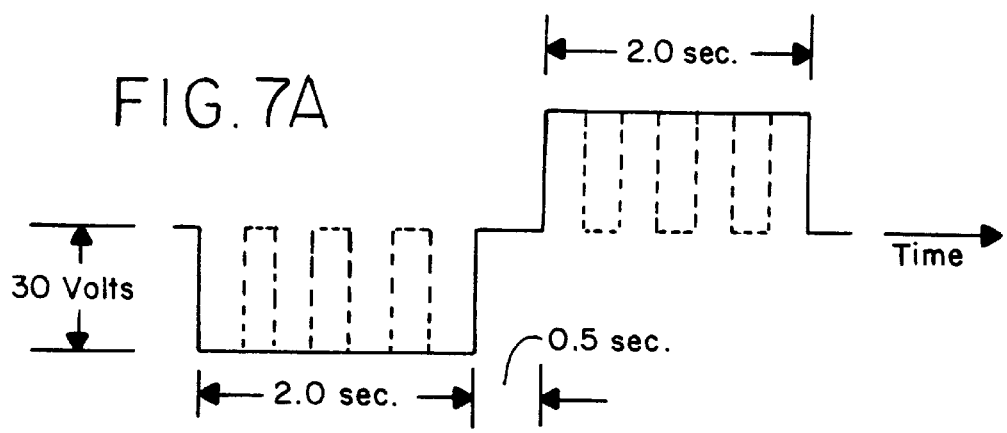
FIG. 7A
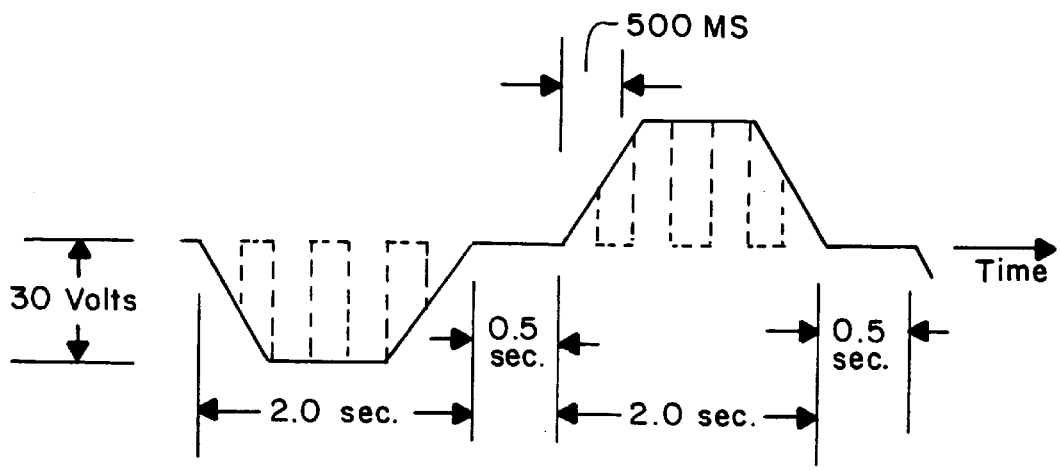
FIG. 7B
FIG. 7C

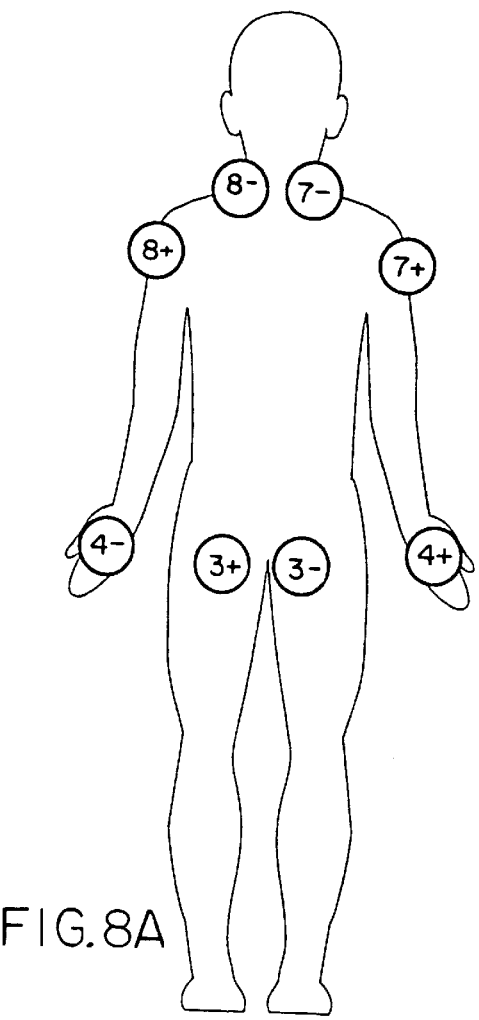
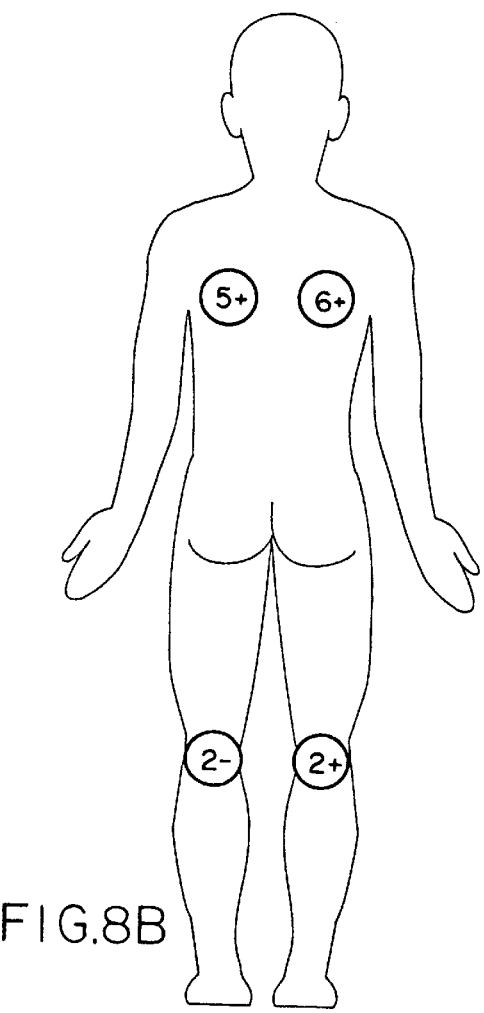
FIG.8A    FIG.8B
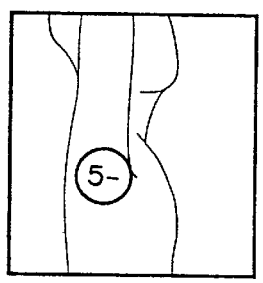
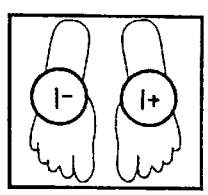
FIG.8C    FIG.8E
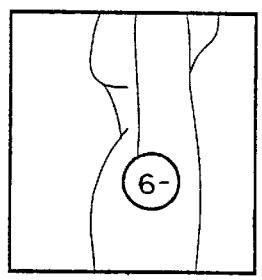
FIG.8D
Legend
| Ch 1 | B+ | R- |
| Ch 2 | Y+ | G- |
| Ch 3 | B+ | R- |
| Ch 4 | Y+ | G- |
| Ch 5 | B+ | R- |
| Ch 6 | Y+ | G- |
| Ch 7 | B+ | R- |
| Ch 8 | Y+ | G- |

Legend

| Ch 1 | B+ | R- |
| Ch 2 | Y+ | G- |
| Ch 3 | B+ | R- |
| Ch 4 | Y+ | G- |
| Ch 5 | B+ | R- |
| Ch 6 | Y+ | G- |
| Ch 7 | B+ | R- |
| Ch 8 | Y+ | G- |

Legend

| Ch 1 | B+ | R- |
| Ch 2 | Y+ | G- |
| Ch 3 | B+ | R- |
| Ch 4 | Y+ | G- |
| Ch 5 | B+ | R- |
| Ch 6 | Y+ | G- |
| Ch 7 | B+ | R- |
| Ch 8 | Y+ | G- |

Legend

| Ch 1 | B+ | R- |
| Ch 2 | Y+ | G- |
| Ch 3 | B+ | R- |
| Ch 4 | Y+ | G- |
| Ch 5 | B+ | R- |
| Ch 6 | Y+ | G- |
| Ch 7 | B+ | R- |
| Ch 8 | Y+ | G- |

Legend

| Ch 1 | B+ | R- |
| Ch 2 | Y+ | G- |
| Ch 3 | B+ | R- |
| Ch 4 | Y+ | G- |
| Ch 5 | B+ | R- |
| Ch 6 | Y+ | G- |
| Ch 7 | B+ | R- |
| Ch 8 | Y+ | G- |

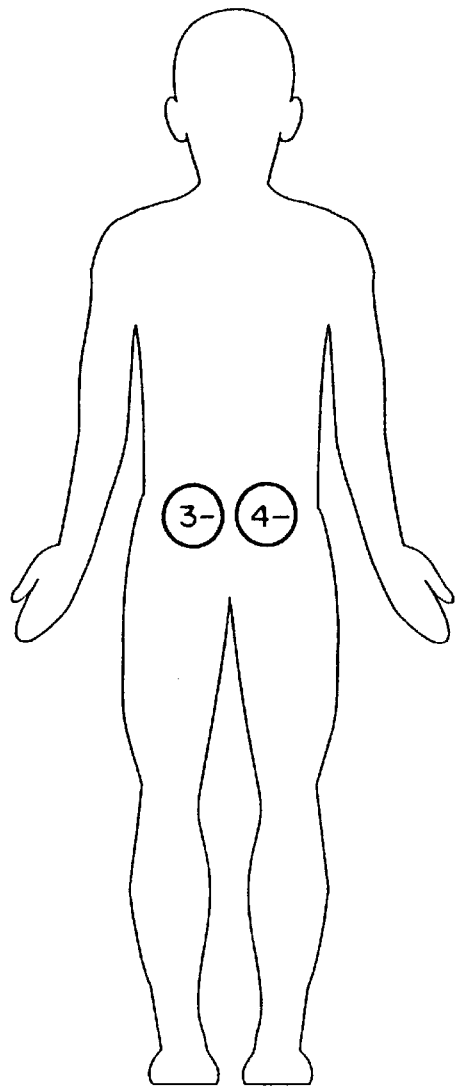
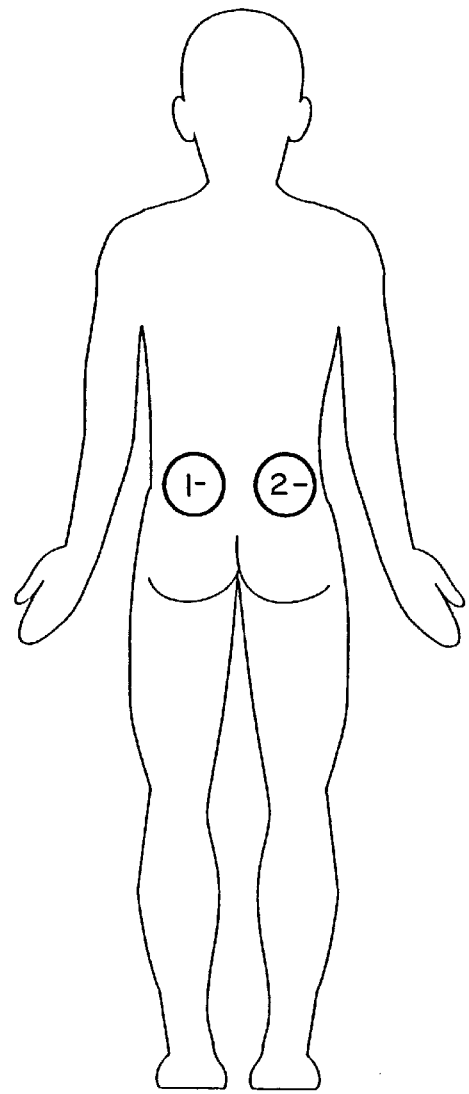
FIG.14A
FIG.14B
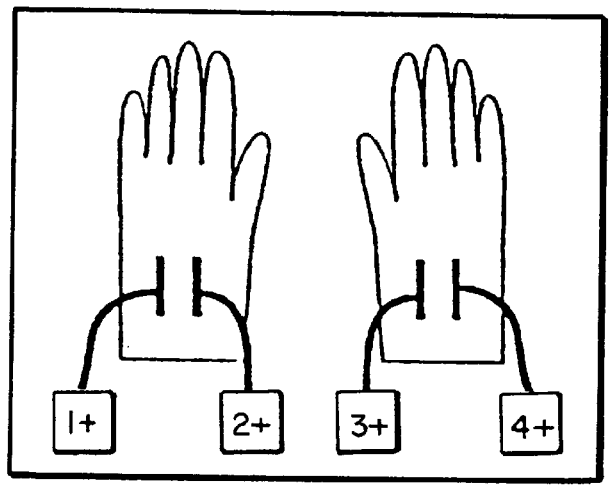
FIG.14C

MULTI-CHANNEL, INTERFERENTIAL WAVE, MICRO CURRENT DEVICE AND METHODS FOR TREATMENT USING MICRO CURRENT

FIELD OF THE INVENTION

The present invention relates to a multi-channel, interferential wave, micro current device that is useful for treatment of edema and other indications and to methods for treating edema and other indications using micro current.

BACKGROUND OF THE INVENTION

The various tissue of mammalian organs all produce small (less than 1 milliamp) direct ("DC") electrical currents. Electroencephalograms and electrocardiograms (EEGs and EKGs, respectively) are measurements of these DC currents in the brain and heart, respectively, of man.

Damage to these and other mammalian tissues produce significant changes in the patterns of these electrical currents which appear to be generated in part by the precise spatial organization of anionic and cationic components of the intra-and-extracellular structures within these organs. The external surface of the skin, for example, is electronegative while the internal base of the skin is electropositive. Like the charge separation between the two poles of a battery, a small current of electricity moves through the dermis or middle layer of the skin (30–100 mV). With injury, this structure is altered and the resistance to electric current flow of the injured tissue is reduced. Intrusion of fluids (blood, serum) into the damaged dermis further reduces this electrical resistance.

Cheng, et al., *Arch. Dermatol.*, Vol. 129, pp. 264–271 (1993), reported an experiment involving the conducting of electrical currents through rat skin submerged in a buffer to literature the effect of electric current on the glycine incorporation into proteins and on the a-aminoisobutyric acid uptake by skin cells. Constant currents from 100 to 600 $\mu A$ ("micro amps") were used during incubation of the rat skin in solution for a period of up to four hours at 37° C. It was reported that, at this low current, the synthesis of ATP was increased. However, at currents over 800 $\mu A$, that effect was lost.

In 1993, Wood, et al.,*Arch. Dermatol.,* 129, pp. 999–1008 (1993), reported the treatment of decubitus ulcers using pulsed, low-intensity direct current ("PLIDC"). A PLIDC instrument (MEMS CS 600, Harbor Medical Inc., Minneapolis, Minn.), an investigational exempt device, was used with a 12 volt battery to provide current breakthrough across the ulcer of 300 $\mu A$ followed by treatment at 600 $\mu A$. The current was pulsed starting negative with a frequency of about 0.8 Hz.

Many cancer patients undergo radiation therapy. Clinically, it is widely known that radiation therapy will lead to edema of irradiated soft tissues, and lymphedema of any irradiated lymphatic tissue. Lymphedema is generally the more serious of these two side effects, because of the overwhelming importance of the patient's lymphatic system to continued immune function and general health.

The lymphatic system is comprised of lymphatic vessels that transport lymph fluid, together with a number of structures and organs that contain lymphatic tissue in a specialized form of reticular connective tissue that contains large numbers of lymphocytes. The stroma framework of lymphatic tissue is generally a meshwork of reticular fibers (fibroblasts) and reticular cells (fixed macrophages), although the thymus gland component of the various lymphatic organs is composed of epithelioreticular tissue.

Lymphatic vessels include lymph capillaries, combined in larger lymph vessels (lymphatics) which resemble veins in structure but have thinner walls and more valves, as well as containing lymph nodes at various intervals throughout the body. the most intense concentration of lymph nodes are found in the face and neck, the arm pits, the thoracic cavity, the intestines and groin, the elbows, and knees. Shallow lymphatics of the skin generally follow veins, while deeper lymphatics generally follow arteries. The lymphatics function to deliver lymph throughout the body and return proteins to the cardiovascular system when they leak out of blood capillaries. Lymphatics also transport fats from the gastrointestinal tract to the blood. Importantly for cancer patients, lymphatic tissue functions in surveillance and defense of foreign cell, microbes and cancer cells. Some lymphocytes (T cells) destroy these invaders directly or indirectly by releasing various substances. Other lymphocytes (B cells) differentiate into plasma cells that secrete antibodies against foreign substances to help eliminate them. The lymph nodes serve as filter of foreign material carried by the lymph, by virtue of their network of reticular fibers. Then macrophages destroy the foreign substances by phagocytosis. The lymph nodes also serve to produce lymphocytes, some of which are carried in the lymph to other parts of the body as part of its immunologic defense system. The spleen, thymus and tonsils are the lymphatic organs which produce B-cells, T-cells, and lymphocytes together with antibodies, respectively, to complete the lymphatic system immunologic defenses.

Lymphedema is the result of blocking lymphatic drainage of the lymph tissue area by the degradation products of cell death. Infiltration of this blocked tissue by macrophages leads to clearing of lymph flow via proteolysis of the occluding proteins over considerable time. However, the necessary repetition of radiation therapy both continues and increases the occlusion of lymphatic drainage in the irradiated area, thus further prolonging the lymphedema, frequently making it a progressively more severe side-effect.

Symptomatically, swelling of limbs (edema, an excessive accumulation of interstitial fluid in tissue spaces) and severe lymphedema (including excessive lymph formation faster than it can be passed into lymphatics, together with increased permeability of blood capillary walls) is particularly pronounced with upper torso irradiation of cancers of the head and neck, lungs, breast and the lymphatic system. Fibrosis of the jaw and neck with excessive fibroblast deposition may even ensue for severe cases of strong and frequent upper body radiation, requiring such patients to be fed with a straw, and virtually immobilizing the patient. Fibrosis of the upper arm may also occur with continuing radiation treatment.

New tumors tend to emerge in the edematous limbs and other lymphatic system and having the opportunity to take root and grow, given the seriously reduced lymph flows, lymphocyte production and ion exchange in these radiation-induced immunologically compromised edematous body parts.

This complex and systemic condition is typically treated with "compression therapy" of different kinds with varying degrees of limited success. Existing modalities of concurrent drug therapy involve a wide variety of bioflavenoids and benzopyrones as vasoconstrictors. These natural products are thought to enhance lymphatic flow by decreasing vascular permeability and increasing microvascular resistance to blood flow. Vasoconstriction can be demonstrated experimentally and it can be shown to be inhibited by inhibitors of adrenaline and norepinephrine (the local tissue "adrenergic" system). These bioflavenoids appear to be able to displace stored norepinephrine from neuronal vesicles and by activation of adrenergic receptors of venous smooth muscle cells. These actions suggest the importance of stimulating the local adrenergic system to improve lymphatic and vascular fluid flow.

Rheumatoid arthritis ("RA") is widely believed to be an auto-immune disease in which the patient has become immunologically sensitive to some antigenic material in their own bodies. The primary symptom of RA is inflammation of the synovial membrane, wherein the membrane thickens and synovial fluid accumulates. The resulting pressure causes pain and tenderness. As lymphocytes and macrophages learn to react to these unknown "self-antigens", they accumulate in the target organ—the synovial tissue, a hydrated sack which functions as a cushion and lubricated "bearing" between the joints of the skeleton. The macrophages release small amounts of nitrous acid, together with released free radicals and with nitrosylate tyrosine residues of various proteins and polypeptides. These materials are strongly cytotoxic and produce a pannus of necrosis within the synovium, which adheres to the articular cartilage. The pannus formation sometimes erodes the cartilage completely. When the cartilage is destroyed, fibrous tissue joins the exposed bone ends. The tissue then ossifies and fuses the joint so that it is immovable, leading to a failure of the targeted joint, thereby crippling the patient in use of the afflicted limb.

New and better devices and methods are needed for treatment of edemas, including lymphedema, rheumatoid arthritis, and other indications.

SUMMARY OF THE INVENTION

The present invention provides a low current, interferential wave, micro current device for application of micro amperes of electrical current through tissue of patients in need of therapy. The device provides about four or more channels for applying micro current to a patient, each channel having two electrodes for completing a micro current electrical circuit through patient tissue. The device comprises a power supply or power source, frequency generator, pulse generator, pulse envelope generator and a controller to provide controlled current in each channel from about 20 $\mu$A to about 200 $\mu$A at up to 300 Hz. Two or more frequencies are used to provide interferential wave forms.

The micro current device of the present invention provides low frequency and amplitude wave forms to aid fluid flow in patient tissue and repair of patient tissue. The device provides pulsed energy envelopes of micro current with a mandatory pause between pulses. The wave forms are preferably modulated by a fifty percent duty cycle square wave.

A method for treating a patient in accord with the present invention comprises: providing multiple pair of electrodes, each pair of electrodes connected to provide a micro current of electricity across patient tissue; positioning about four or more, preferably eight, pairs of electrodes on the patient; providing a controlled current from about 20 $\mu$A to about 200 $\mu$A in each channel at a frequency of up to 300 Hz; providing at least two different frequencies to different channels to provide an interferential wave form; and providing pulsed energy to the patient using a wave form envelope with a mandatory pause between pulses.

Preferably, the wave form is modulated with a fifty percent duty cycle square wave. Positioning the electrodes at centers of lymph nodes can increase drainage in the lymphatic system. Improvement in lymphedema, edema, fibrosis and fibromylagea, as well as other indications, can also be found after micro current treatment in accord with the present invention. Thus, the method of the present invention can provide benefit to a patient having any indication susceptible to improvement by micro current therapy.

BRIEF DESCRIPTION OF THE DRAWINGS

FIGS. 6D–6F illustrate pulse wave form envelopes useful for micro current treatment in accord with certain embodiments of the present invention.

FIGS. 7A–7E illustrate modulated (dotted lines) wave form envelopes having differing leading and trailing edges useful for micro current treatment in accord with certain embodiments of the present invention.

FIGS. 8A–8E illustrate the placement of pairs of conductive pads or electrodes for micro current treatment of the whole body in accord with certain embodiments of the present invention.

FIGS. 14A–14C illustrate the placement of conductive pads or electrodes for use in combination with the gloves of FIG. 13 for micro current treatment of a middle or lower portion of the body in accord with certain embodiments of the present invention.

DETAILED DESCRIPTION OF INVENTION INCLUDING PREFERRED EMBODIMENTS

The invention will be further described with reference to the embodiments illustrated in the attached drawings. In one embodiment, a pulsed, micro current, interferential wave device of the present invention has eight channels. A microprocessor controls the wave form width, amplitudes and polarity of each pulse and provides a pause between pulses. The wave form can be modulated by a frequency from about 0.1 to about 300 Hz and provide electrical current from about 20 $\mu$A to about 180 $\mu$A in each channel, independently, as controlled by the microprocessor. Each pulse can be positive, negative, or the pulses can alternate between positive and negative. The wave form can be modified to provide any shape for the leading and trailing edges.

Figure 1:
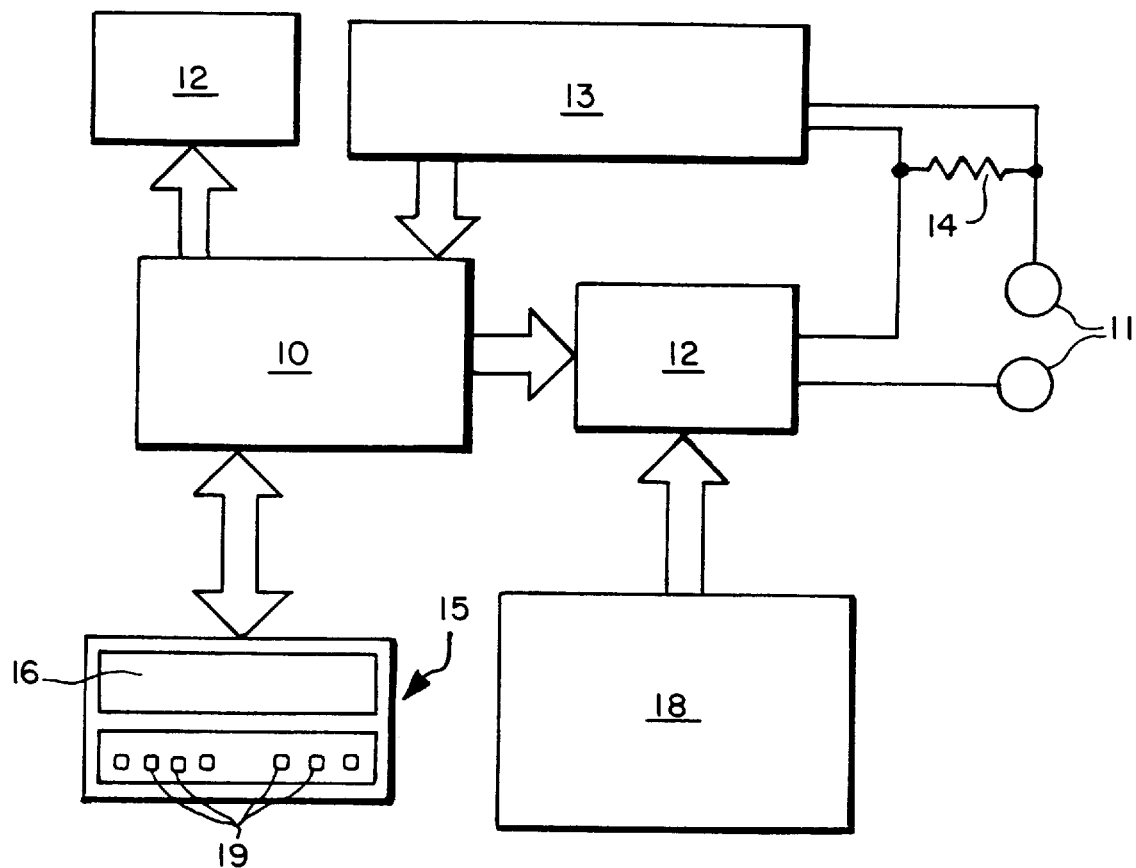
FIG. 1 is a block diagram of one embodiment of a pulsed, micro current device of the present invention illustrating one channel.

As illustrated in FIG. 1, one embodiment of the invention comprises a microprocessor control unit 10 ("MCU") controlling analog output circuitry 12 and instrumentation circuitry 13, a power supply 18, an audio speaker 17 and a control panel 15 with a liquid crystal display 16 ("LCD") and keyboard push buttons 19. The output leads 11 for only one of eight channels is illustrated in block diagram of FIG. 1.

The microprocessor of the control unit is a low power 8 bit microprocessor leaving provisions for random access memory ("RAM"), read-only memory ("ROM"), analog to digital conversion ("ADC"), digital to analog conversion ("DAC"), computation, time-keeping and communication.

The power supply is a switching power supply that can generate plus or minus 32 volts for a high voltage output operational amplifies (not shown), plus or minus 9 volts for an instrumentation operational amplifier, plus 5 volts for the microprocessor. The power can be supplied by batteries having a nominal working voltage of 12 volts or by any other source. The power is turned on by a push button and preferably turns off automatically after about six minutes, if no wave forms are being generated. The microprocessor also can control the on-off status of the power supply.

The analog output circuitry is used to supply the current across a channel under control of the microprocessor control unit. The circuitry is illustrated in more detail in FIGS. 16–26, which are described below. The output stages are op amps in a voltage controlled constant current configuration with a maximum current capability of 180 $\mu$A at 30 volts. The MCU controls the voltage with a DAC which connects to the op amp to set the output current of the op amps. The DAC allows programmable ramp up of the current. An in-line voltage multiplier controls the on/off status and polarity of the output stage. The output current flow is controlled with the op amp circuit only, after the voltages are set.

The instrumentation circuitry is a high impedance circuit that is the microprocessor to measure output current and output voltage as seen by the patient. The circuit is illustrated in more detail in FIG. 21, and described below. The output current is sensed with a high impedance circuit connected directly to the output section. The output voltage is sensed by measuring the voltage directly through a high impedance voltage divider. These measurements are used for display purposes only and are not used to control the output.

The control panel with LCD provides means for selecting desired parameters and pre-programmed treatment settings that are groups of parameters predetermined for particular treatments, and for displaying various treatment parameters such as time, current, voltage, etc. Convenient buttons are used for turning on the device and entering parameters and settings.

The audio speaker is a preferred means to provide audible feedback to the user, confirming button panels and current flow. The frequency of the tone varies with the amount of current—e.g., higher frequency for higher current.

Variations in power supply will not prevent the unit performing to specification. The unit will perform to spec from 9 volts to 15 volts. If the voltage were to go above 15, or below 9, the micro processor will not perform as intended; however, this will not harm the patient or the device electronics. In fact, there would be no output. If all of the necessary events were to occur simultaneously, thereby causing the unit to malfunction, the device is designed to limit the maximum possible current to only 600 micro amperes (at 30 volts).

In addition to the above power limitations of the device, an additional fail safe feature continuously monitors the battery voltage levels. When the voltage level has dropped below 12 volts, the LCD display will remind the operator to replace the batteries.

Figure 2:
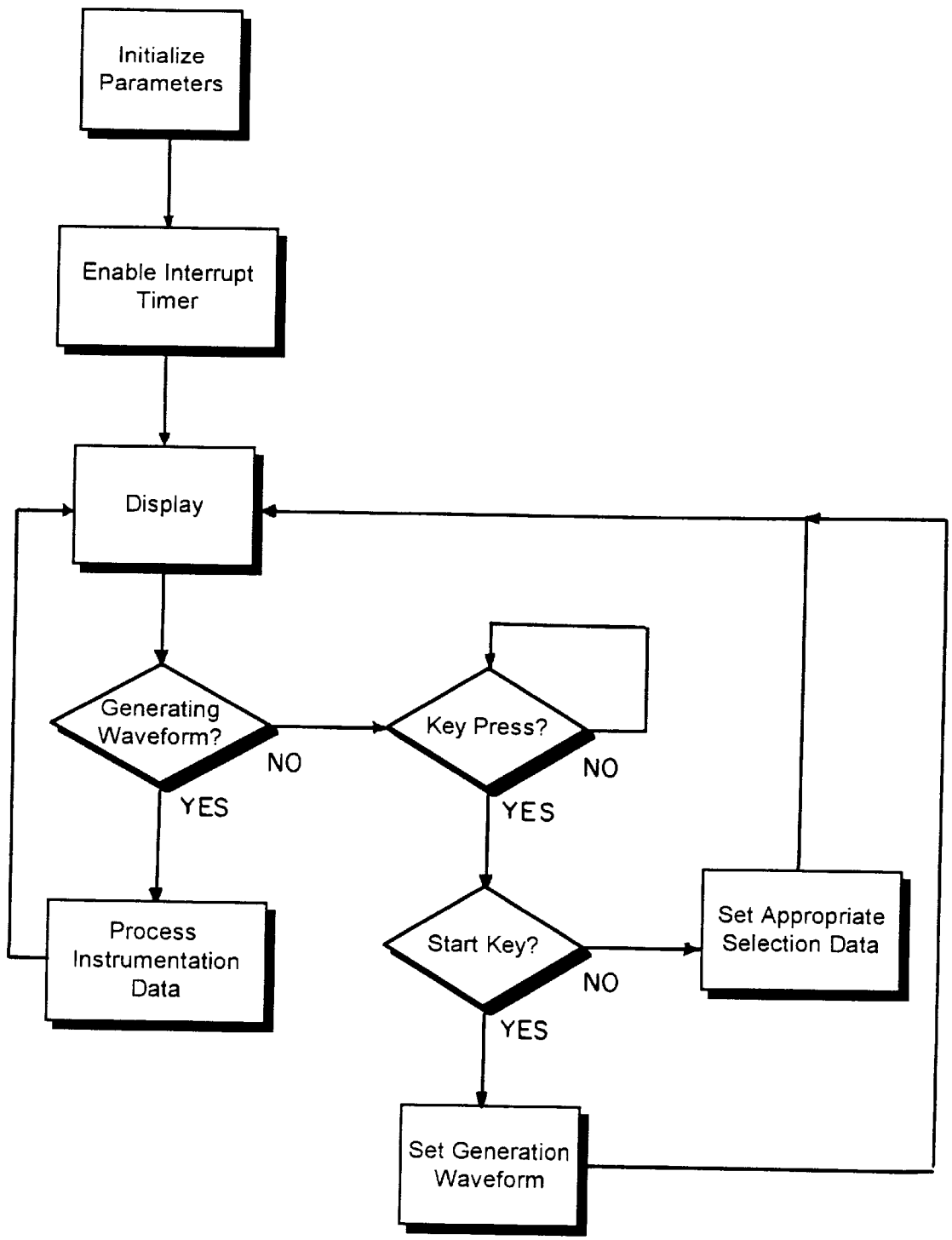
FIG. 2 is a flow chart for the main control program run by a microprocessor for a device in accord with the present invention.

The MCU is programmed with a main program as illustrated by the flow diagram in FIG. 2, which runs in the foreground and timer interrupt program that runs in the background. The main program load initial parameters, starts the timer interrupt program, writes to the LCD displays, sets all wave form and current generation off, and sets sound off.

Figure 3:
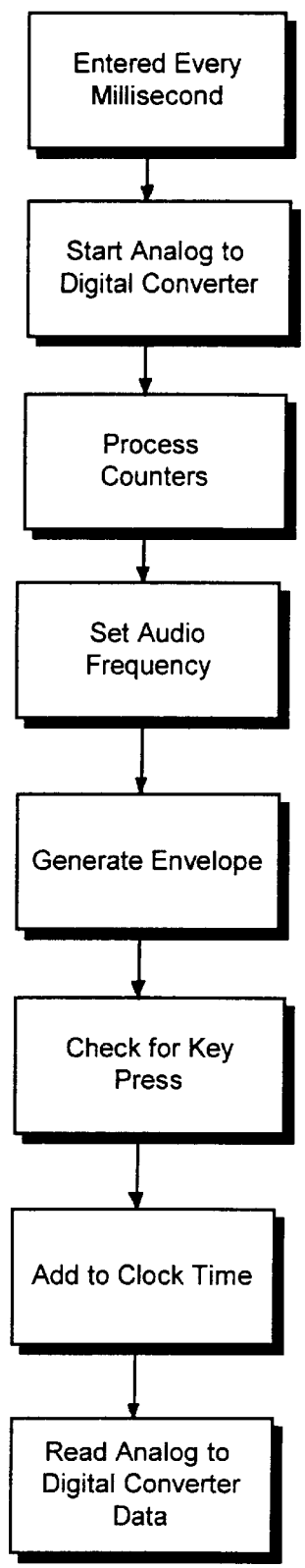
FIG. 3 is a flow chart for an interrupt timer program run by a microprocessor for a device in accord with the present invention.

There also is one timer interrupt program, as illustrated by the flow diagram in FIG. 3, input to receive operation input. After necessary selections have been made and the start button pressed, the unit begins output current generation. The data display is generated by the main program from data as stored by the interrupt timer program on a item available basis. Wave form frequency generation is handled outside by hardware timers. Envelope generation is handled by the interrupt timer program.

Figure 22:
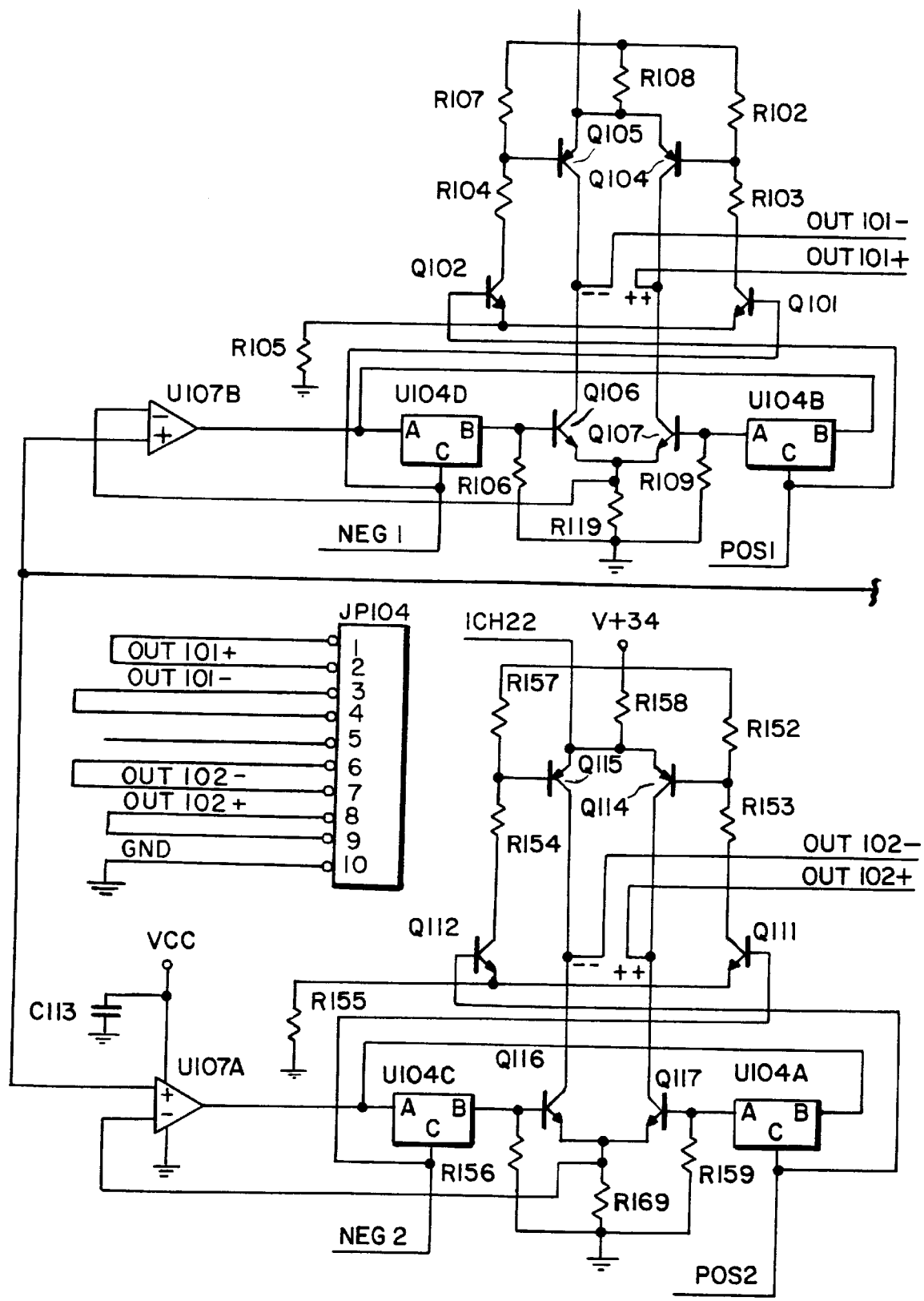
FIG. 22 illustrates a H-Bridge circuit for two channels that outputs a user selected amount of current for a micro current device in accord with the present invention.

The microprocessor can produce wave forms with selected envelopes, modulating frequencies, and polarity. Each channel can be independently controlled. Each output channel is a separate operational op amp circuit, with signal wiring physically isolated from the other channels using 1 Meg ohms between channels. The output channel circuitry is shown in FIG. 22.

The electrical output of the micro current device is a wave form, representing the current as measured across a 10 k ohm resistor—(see resistor 14, FIG. 1). The wave form is typically a complex wave form. In general, all wave forms consist of a selectable predetermined wave form envelope, which is then modulated with a 50% duty square wave, of the frequency selected.

Figure 4A:
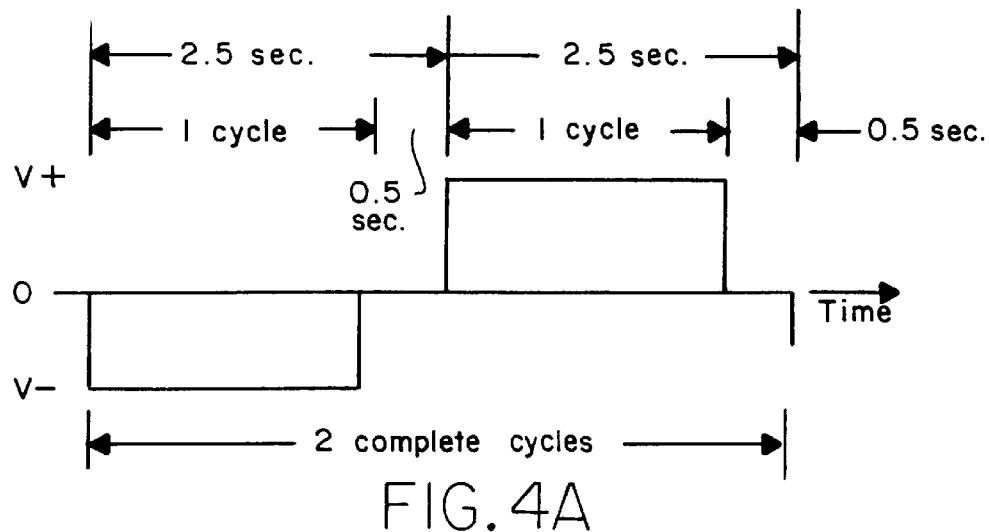
FIGS. 4A–4C are square wave form envelopes and modulation useful for micro current treatment in accord with certain embodiments of the present invention.
Figure 4B:
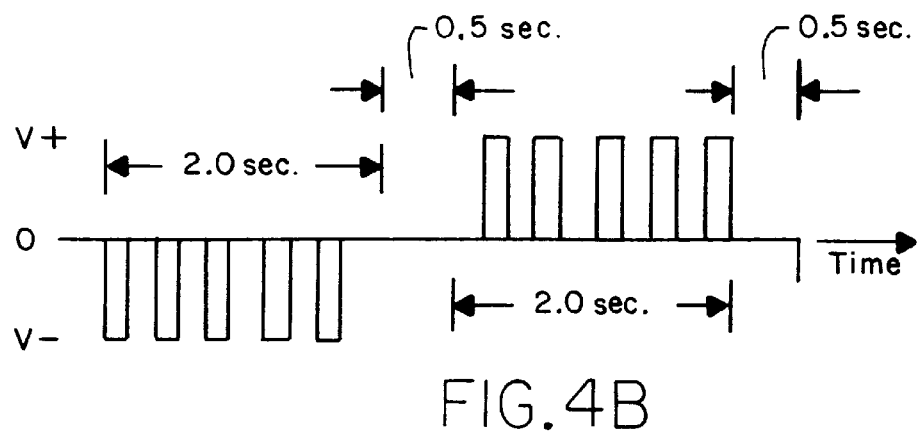
Figure 4C:
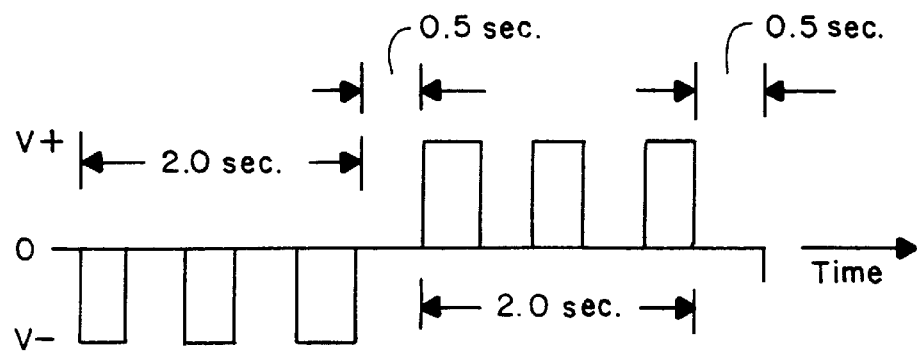

With reference to FIG. 4A, a preferred standard wave form (of two complete cycles) consists of an envelope of 2.0 second negative square wave with a 0.5 second pause and then a positive wave form for 2.0 seconds. For example, this wave form envelope can be modulated by a 2.2 Hz frequency 50% duty cycle signal (See FIG. 4C). The modulating frequency of 2.2 and 1.3 Hz signal is referred to as the frequency of the output wave form is selectable, i.e., other modulation frequencies can be selected. The wave shape envelope does not change due to frequency and is always fixed at 2.0 second square wave, with a 0.5 second pause, then another 2.0 second square wave with a 0.5 second pause, etc.

As used, herein a pulse is one cycle, e.g., a wave shape envelope of negative polarity or a wave shape envelope of positive polarity.

Preprogrammed into the MCU are six selectable wave shape envelopes.

Figure 5A:
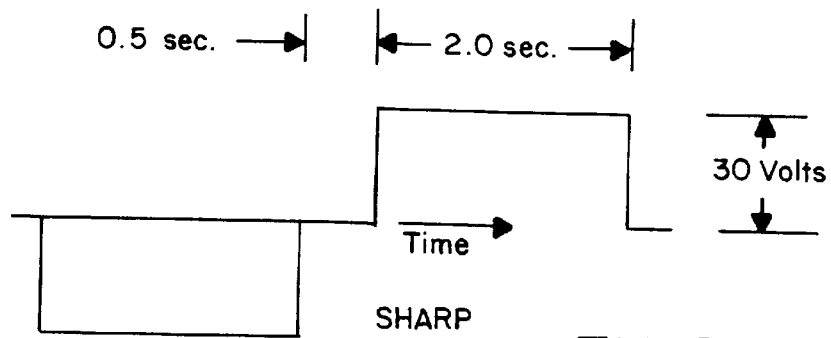
FIGS. 5A–5C illustrates the modification of the leading and trailing edges of wave form envelopes useful for micro current treatment in accord with certain embodiments of the present invention.
Figure 5B:
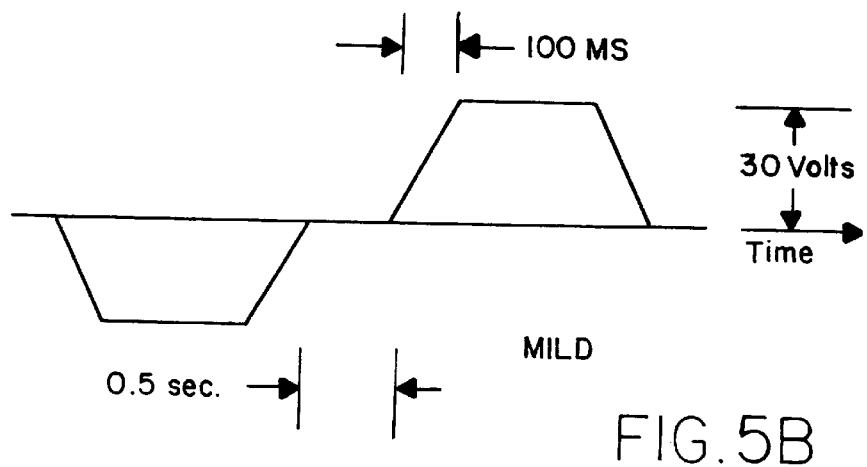
Figure 5C:
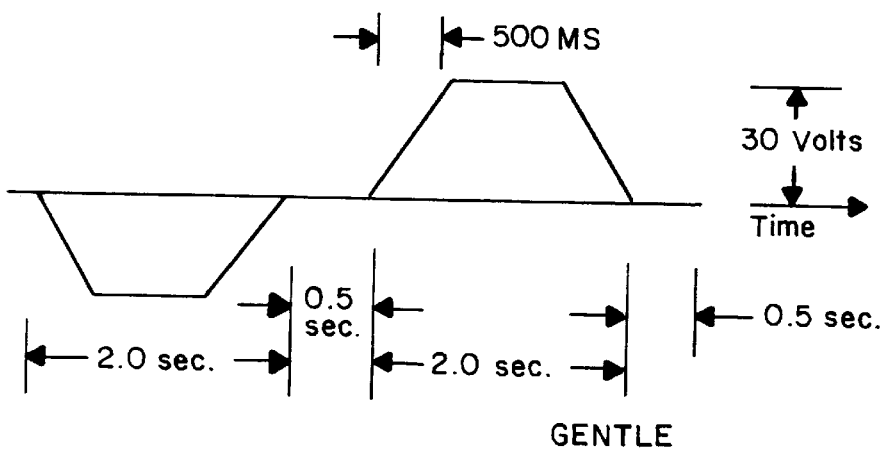
Figure 5D:
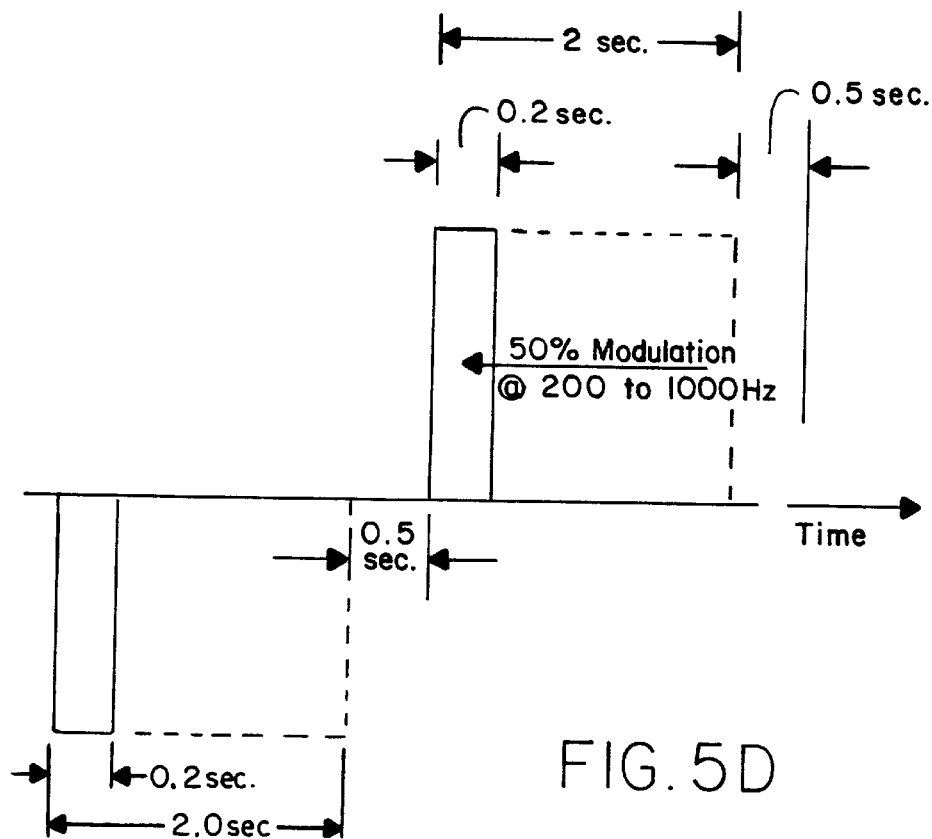
Figure 5E:
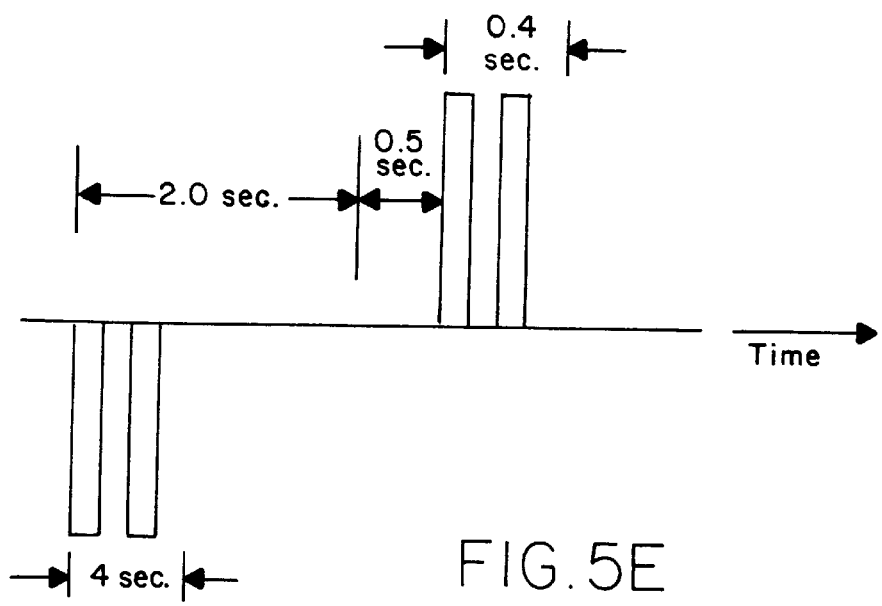
Figure 5F:
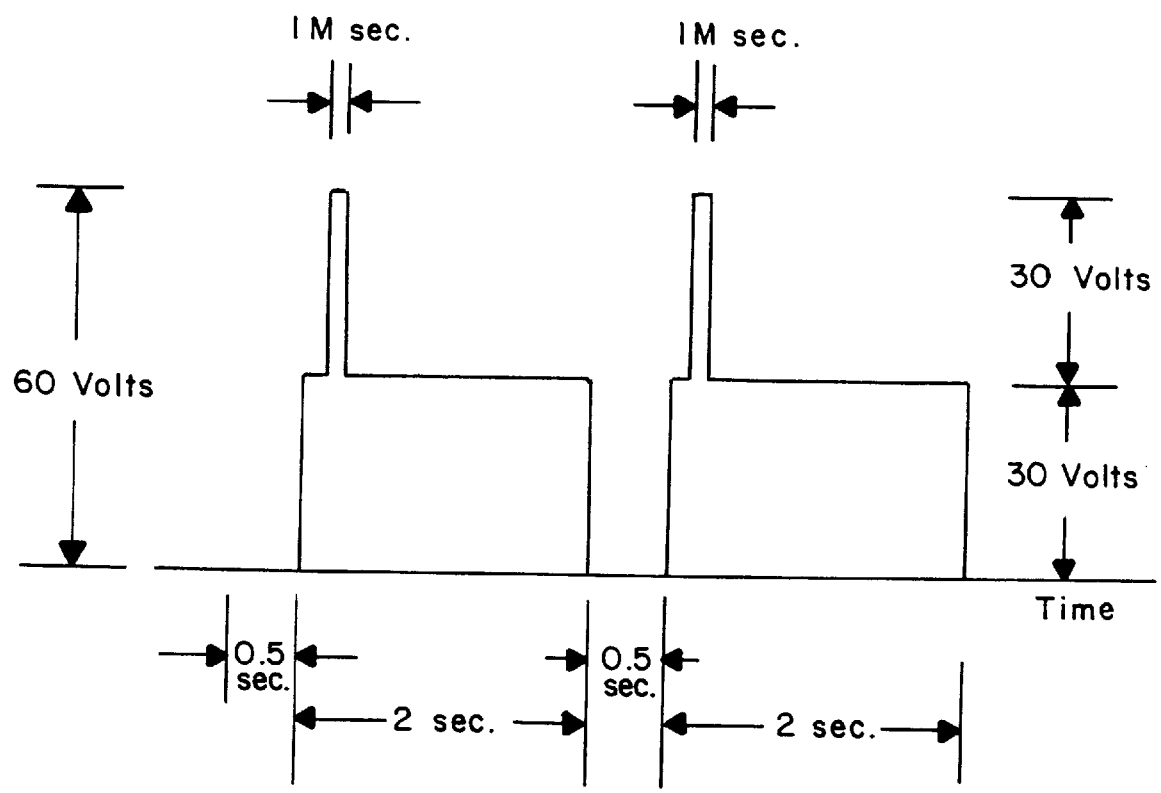

The "sharp edge" envelope consists of a minimum rise time leading and trailing edge (approximately 1 millisecond) and is shown in FIG. 5A. The "mild edge" envelope consists of a medium rise and fall time of about 100 milliseconds ("Ms") and is shown in FIG. 5B; the "gentle edge" envelope consists of a 500 Ms rise and fall time as shown in FIG. 5C. The "sharp pulse" envelope is a single sharp pulse per cycle of 0.2 seconds wide as shown in FIG. 5D. The "double sharp pulse" envelope is two sharp pulses per cycle of 0.2 seconds wide, as shown in FIG. 5E. Generally, the sharp pulses for the pulse envelope are from about 0.1 to about 0.5 second. In the "pulsed sharp edge wave form" envelope, each pulse is a 30 volt 2 second wide sharp edge envelope with a 1 ms wide 30 volt pulse riding on the sharp edge envelope as shown in FIG. 5F.

Of course, the pulse width or cycle time can be varied as well as the length of the pause between cycles. Typically, the pulse width will vary from about 0.5 to about 5.0 seconds. The length of the pause between cycles (or pulses) will generally be from about 10% to about 25% of the pulse. A preferred time period for the pause is about 0.5 second. However, there will be variations in such time periods according to the treatment regimen.

The wave form envelope can also be varied to provide any shape wave form desired.

Figure 6A:
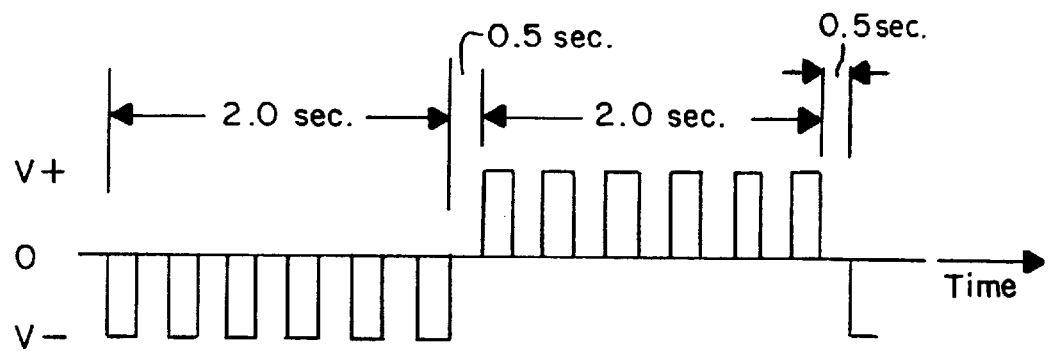
FIGS. 6A–6C illustrate modulated wave form envelopes having differing polarity useful for micro current treatment in accord with certain embodiments of the present invention.
Figure 6B:
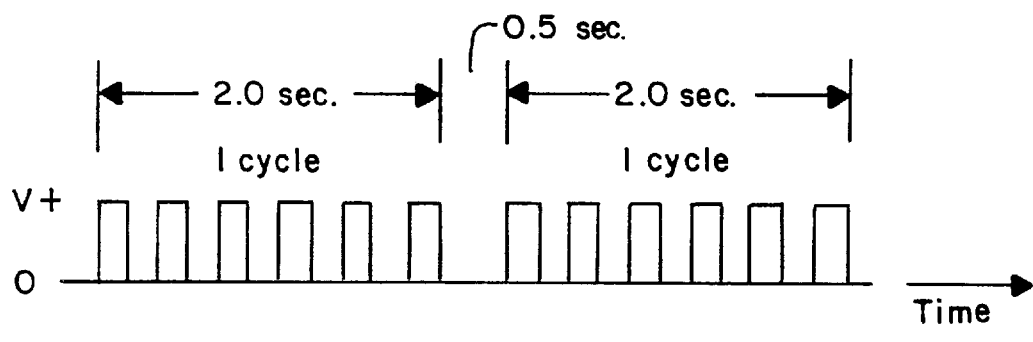
Figure 6C:
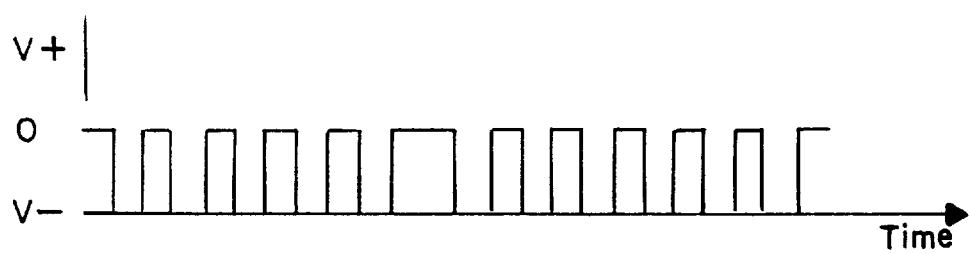

The MCU provides the user with the selected polarity or preprogrammed wave forms as illustrated, e.g. in FIG. 6A (alternating), FIG. 6B (positive) and FIG. 6C (negative) respectively. These are the only selections available. The selected polarity is indicated on the LCD.

In one embodiment, the leading edge of the wave can be selected as the SHARP, MILD, GENTLE, PULSE STANDARD, DOUBLE PULSE and PULSE SHARP envelope. Each wave form envelope has representative differences in the rise time of the leading and trailing edges of the square wave. See FIG. 5A–5F. However, other wave form shapes can be programmed.

The current wave shape form will be the same as the voltage wave shapes form, as illustrated in FIG. 5A–5F, regardless of the current flow, from 40 to 180 micro amperes for the described embodiment. The constant current circuitry maintains the programmed current for the various wave forms shown under various loads from 500 ohms to 10 kilohms and to 50 kilohms. If the current is conducting, the percentage of programmed current flow is displayed on the LCD micro amperes with numerical percentage value along with bar graph indicating 10% for each bar or arrow. For a 60 micro ampere conduction of a programmed value of 100 micro amperes, the declined percent would show 60% and 6 out of 10 arrows or bars will be shown. Each pair of the 8 channels can be monitored two at a time. The LCD will also display the percent of full scale in numeric that the unit is conducting.

Figure 7D:
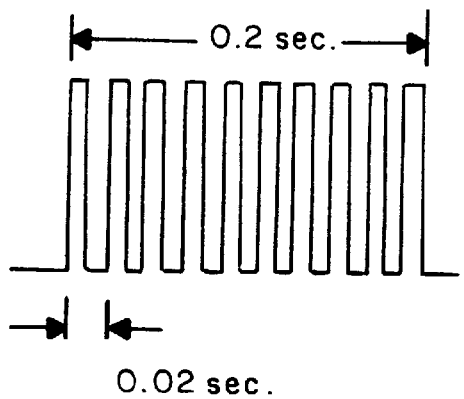
Figure 7E:
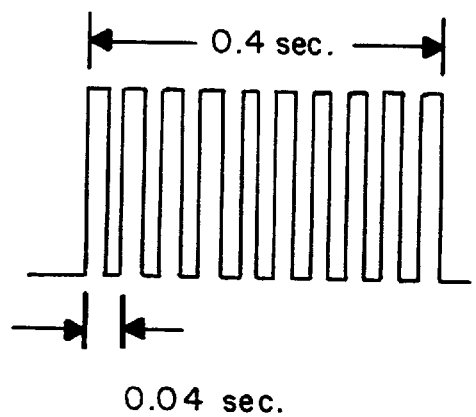

The output frequency refers to the modulating frequency of the pulse envelope. Preferably, modulating frequencies have a 50% duty cycle. The frequency adjustment range on the device is from 0.3 Hz to 300 Hz. The selected frequency is displayed on the LCD screen. FIGS. 7A–7C illustrated a sharp, mild and gentle wave shape envelope modulated by a 0.5 Hz 50% duty cycle wave form square wave. FIGS. 7D and 7E illustrated the pulse ad double pulse envelope modulated by a 50 Hz and 25 Hz 50% duty square waves, respectively. FIG. 7F illustrates the pulsed shape wave form envelope modulated by a 5 Hz 50% duty cycle square wave.

Figure 23:
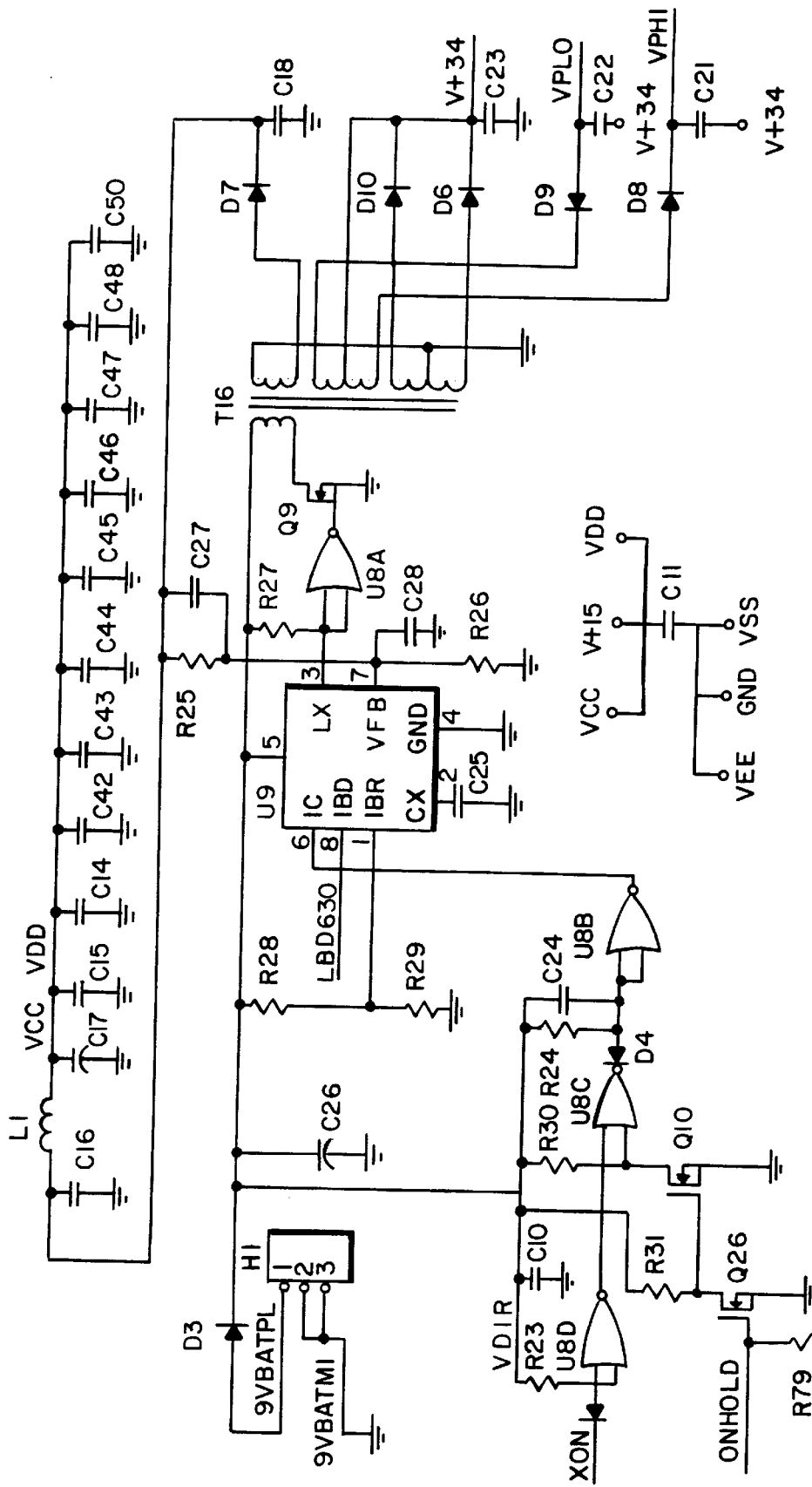
FIG. 23 illustrates a power supply circuit for batteries for a micro current device in accord with the present invention.
Figure 24:
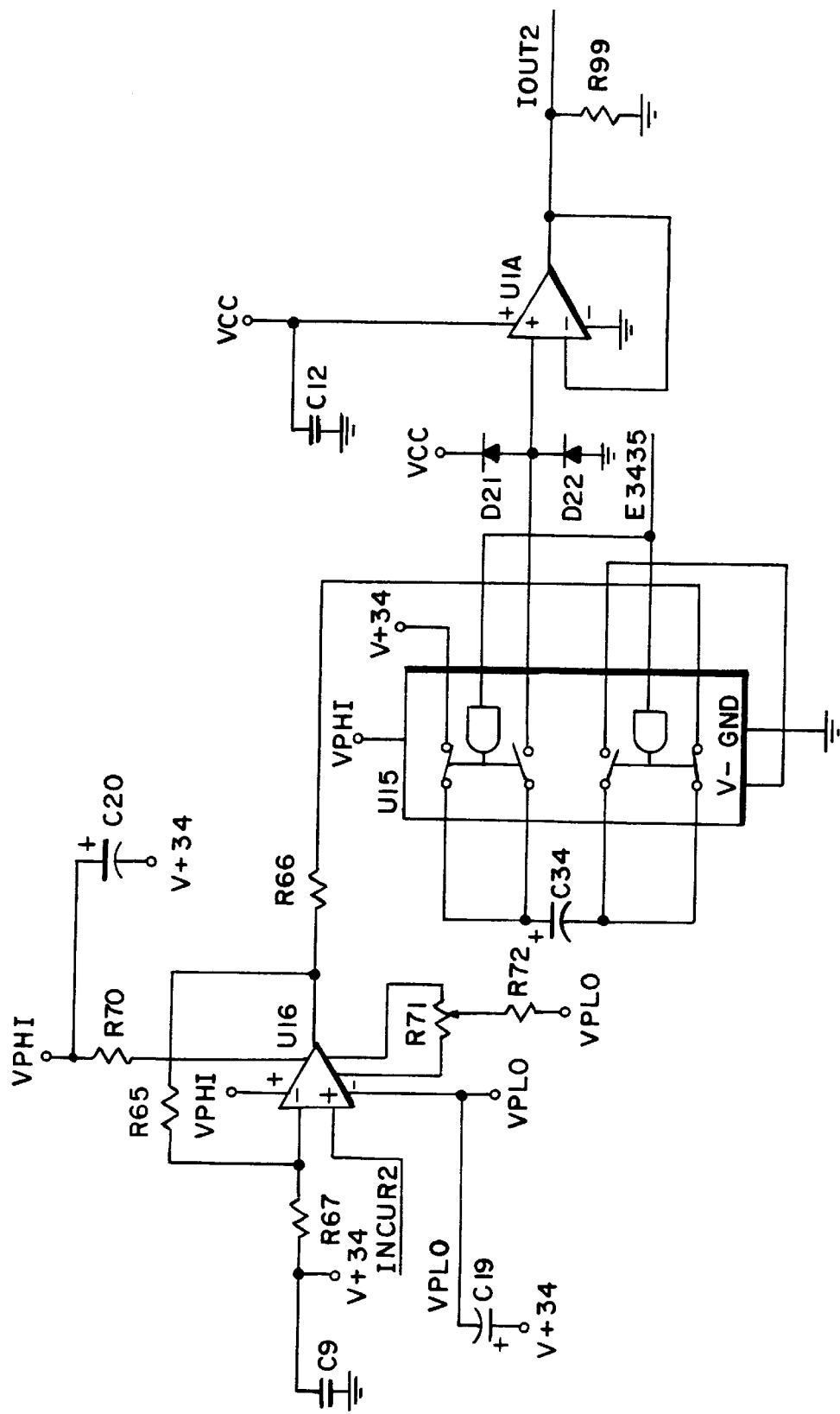
FIG. 24 illustrates a second instrumentation circuit that amplifies signals and makes conversions for the LCD for the B side of the channel for a micro current device in accord with the present invention.

The electrical circuits for the embodiment of a micro current device described above are illustrated in FIGS. 16A–26. The power supply circuit (FIG. 23) provides the necessary operating voltages from a group of eight "D" cells, nominally +5 volts for the computer related circuits, +32 volts for the H-Bridge circuits, and +23 and +41 volts for the instrumentation circuitry. This low power switching power supply is started by pressing the RESET key (buttons 19, FIG. 1) on keyboard of the user panel 15. A timing circuit is activated by the RESET key to turn on the unit and energize the regulator chip U9 (FIG. 23). Regulator chip U9 controls a MOSFET switch Q9 through an inverter buffer gate U8A which provides the transformer T1 primary pulses. Transformer pulses are rectified and filtered to provide the correct required voltages. The power supply will stay on until it is powered off by the MCU 10 (FIG. 1). Alternative power sources can be used as is well known to those skilled in the art.

Figure 25:
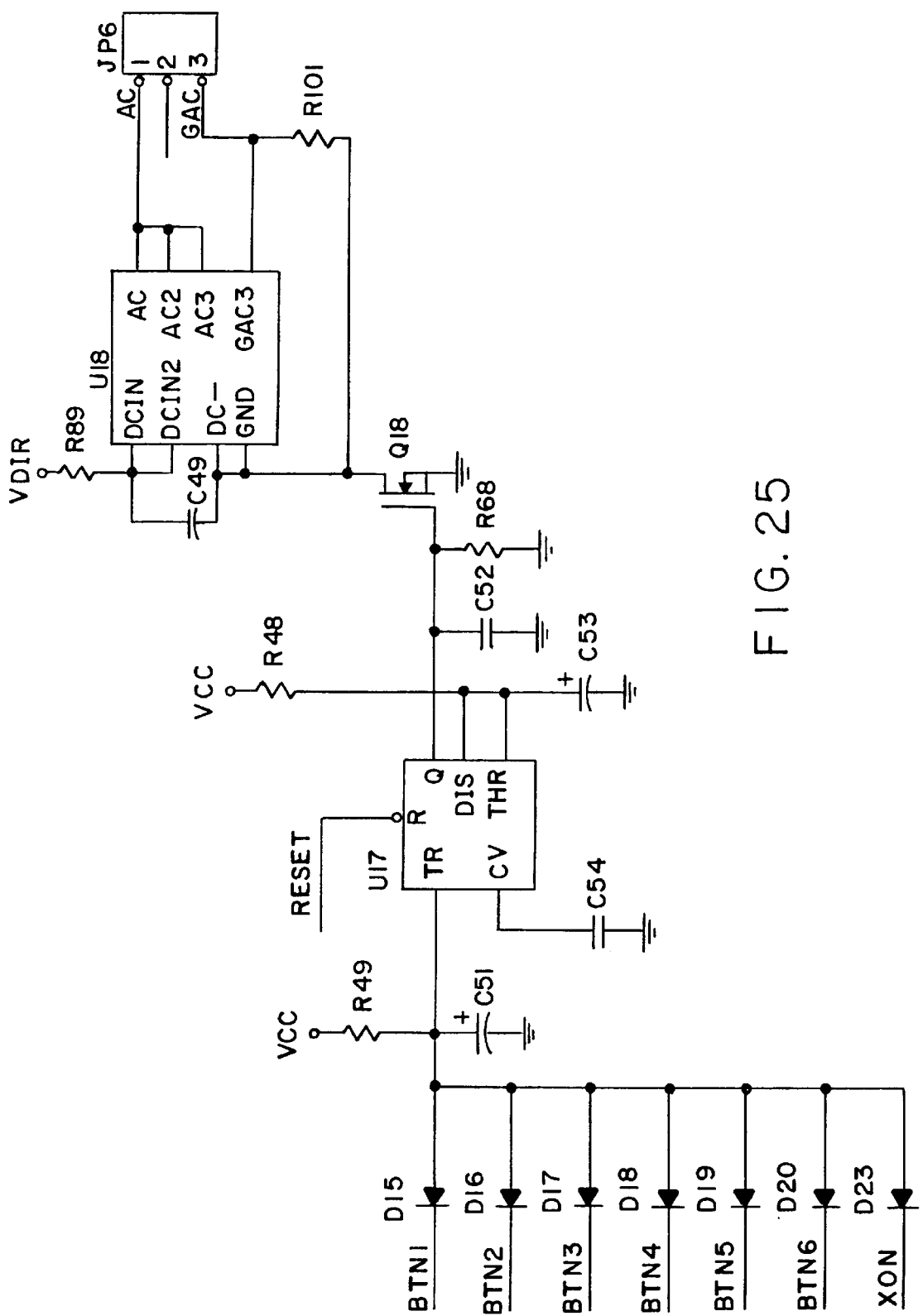
FIG. 25 illustrates a timing circuit and DCAC converter for a micro current device in accord with the present invention.
Figure 26:
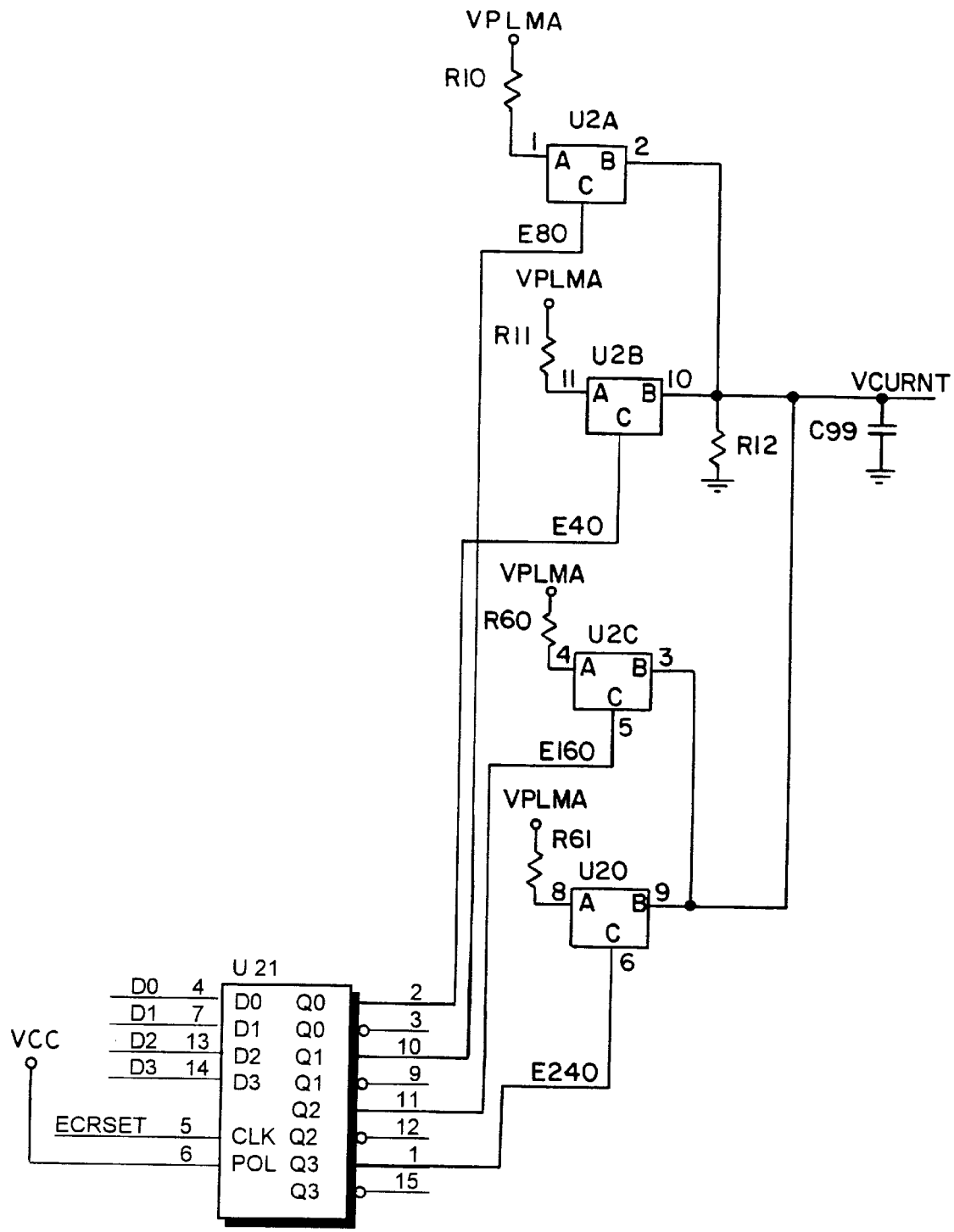
FIG. 26 illustrates H-Bridge polarity and amplitude control circuitry for a micro current device in accord with the present invention.

The MCU 10 (see U3 in FIGS. 16A–16B) is the heart of the unit and supplies the intelligence to run the unit. In addition to control functions, the MCU takes inputs from the keyboard push buttons 19 (using the circuitry illustrated in FIG. 20) and provides output to the user on the LCD. The LCD contains an electroluminescent backlight unit which, when lighted, makes the screen easier to read. The voltage to operate the backlight unit is provided by the DC to AC converter U18 (FIG. 25). Pressing any key or button 19 (other than RESET) causes the backlight to light. The timing circuit (U17, FIG. 25) causes the backlight to stay on for a maximum of about 30 seconds.

The MCU sets the H-Bridge circuits (illustrated in FIG. 22) to provide a user selected amount of current. The current is controlled in a constant mode by the H-Bridge feedback circuits. In this embodiment, the current can be selected in five discrete steps—40, 80, 100, 160 and 180 µA (see FIG. 26) by setting the control voltage to the H-Bridge op amp U107. This is accomplished through the associated op amp feedback circuitry. Current cannot exceed the selected set value or 180 µA under any circumstances using the illustrated circuitry.

Figure 16A:
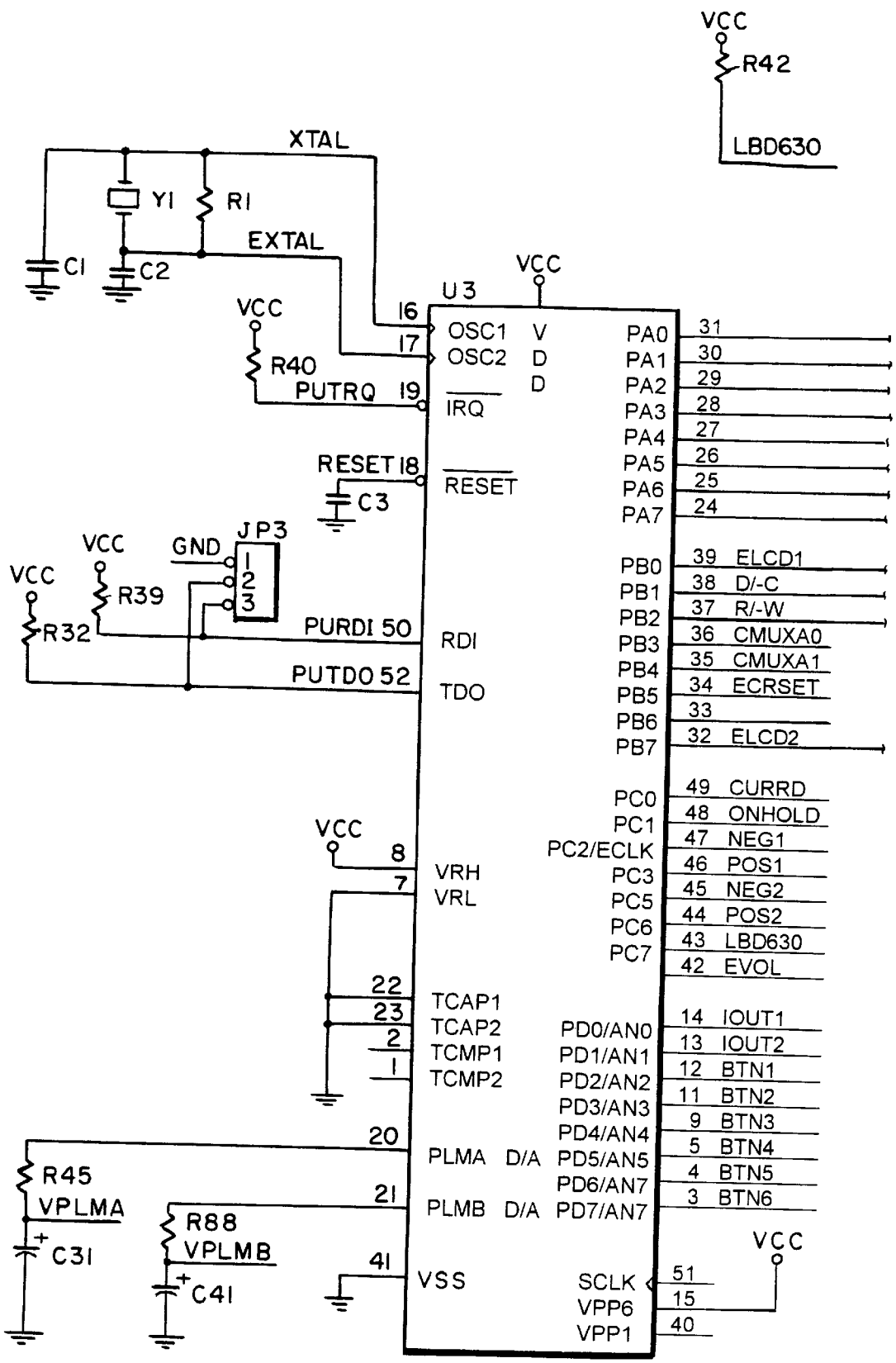
FIGS. 16A–16B illustrates a circuit illustrating the input and output of the microprocessor U3 for a micro current device in accord with the present invention.
Figure 16B:
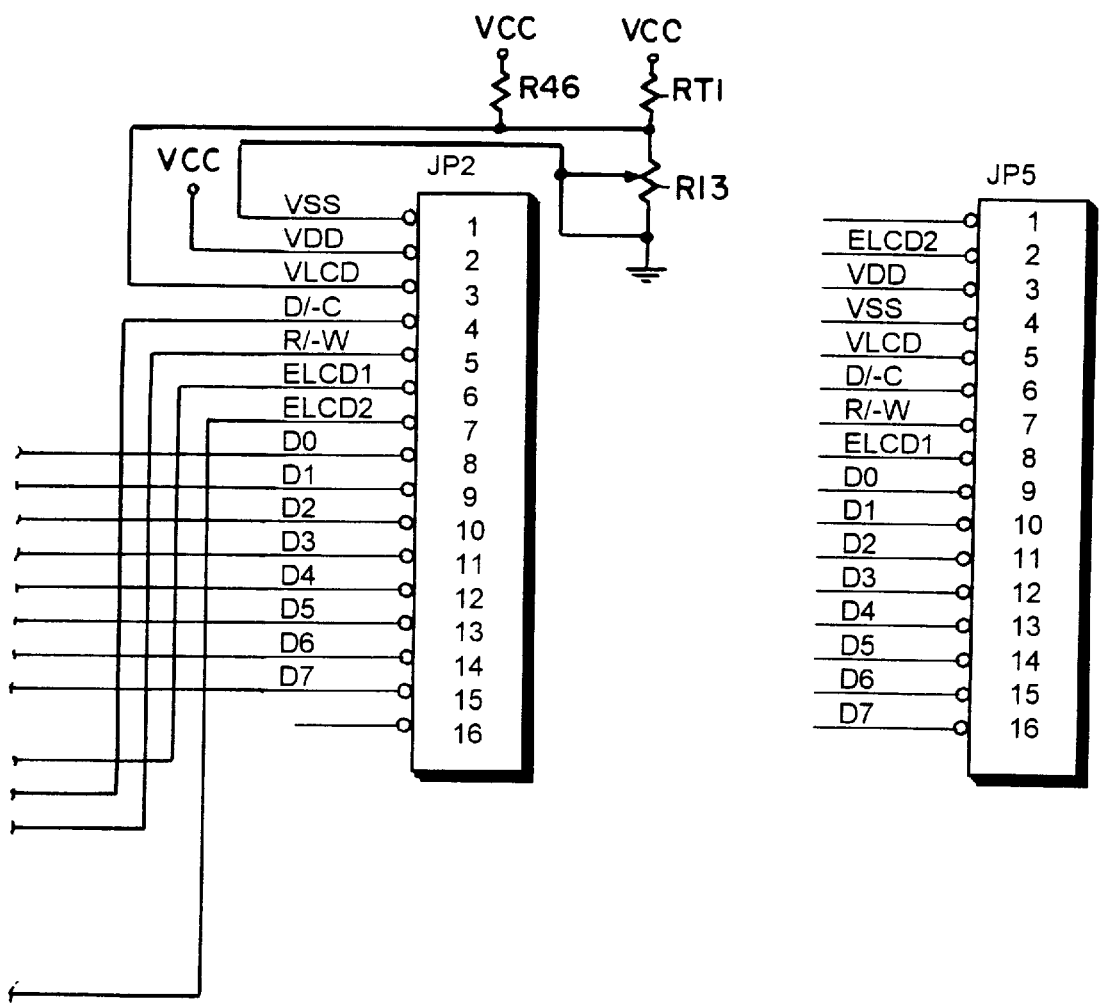
Figure 17:
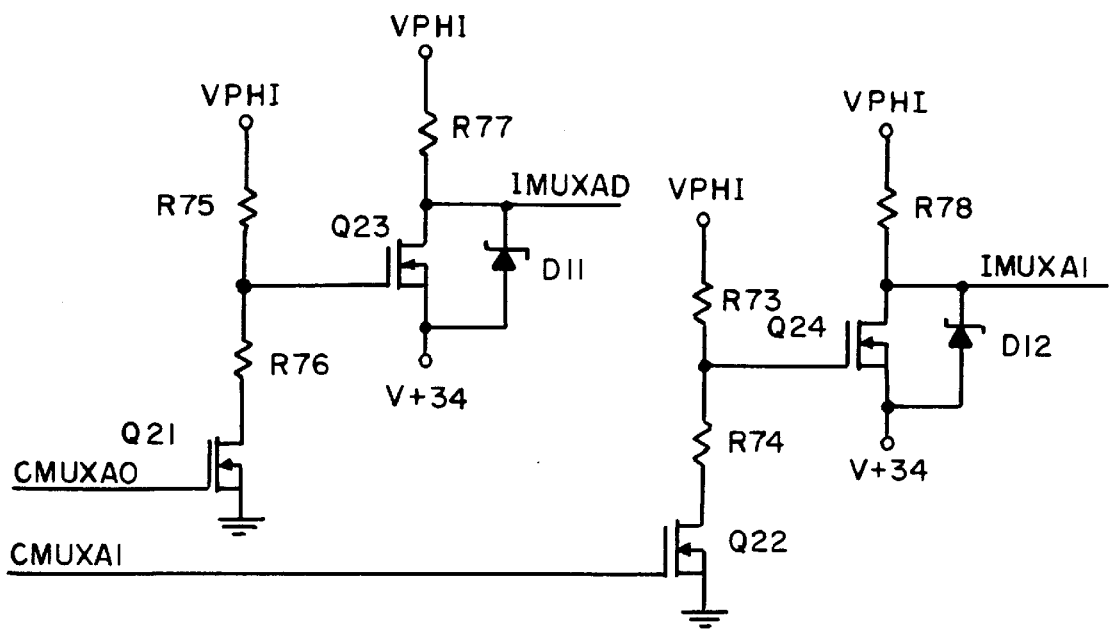
FIG. 17 illustrates a voltage level control circuit that provides voltage conversion to control an analog multiplex circuit operating at high voltage for a micro current device in accord with the present invention.
Figure 19:
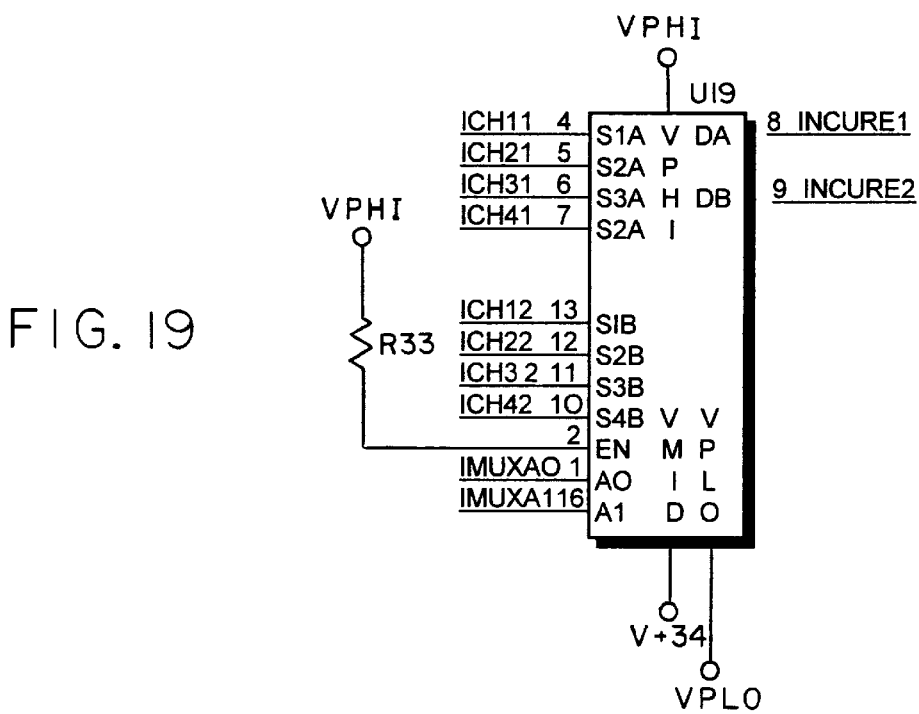
FIG. 19 illustrates a data multiplex circuit that directs a single channel of data to the instrumentation unit for a micro current device in accord with the present invention.
Figure 18:
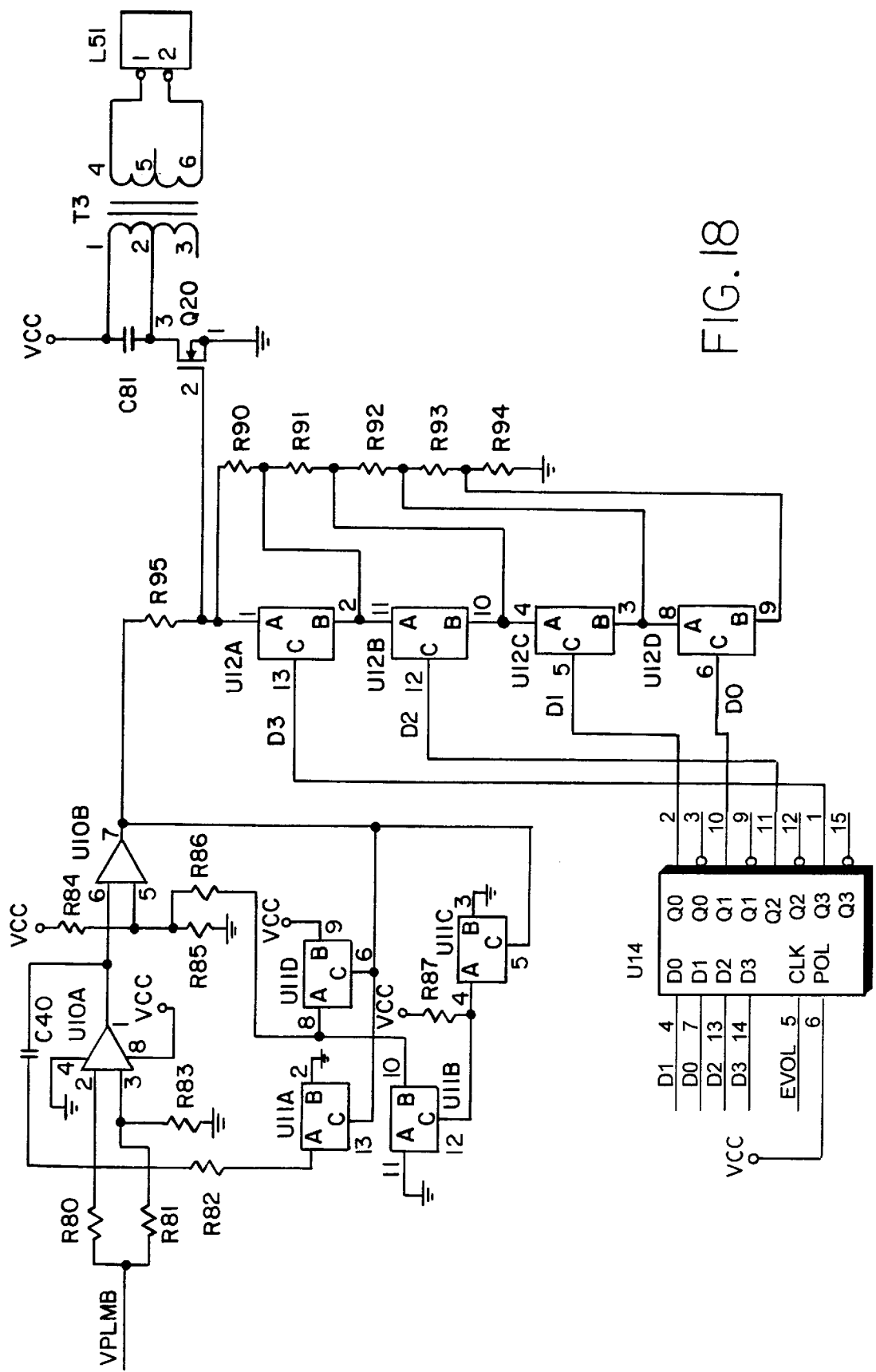
FIG. 18 illustrates a circuit that produces the tone for a micro current device in accord with the present invention.
Figure 20:
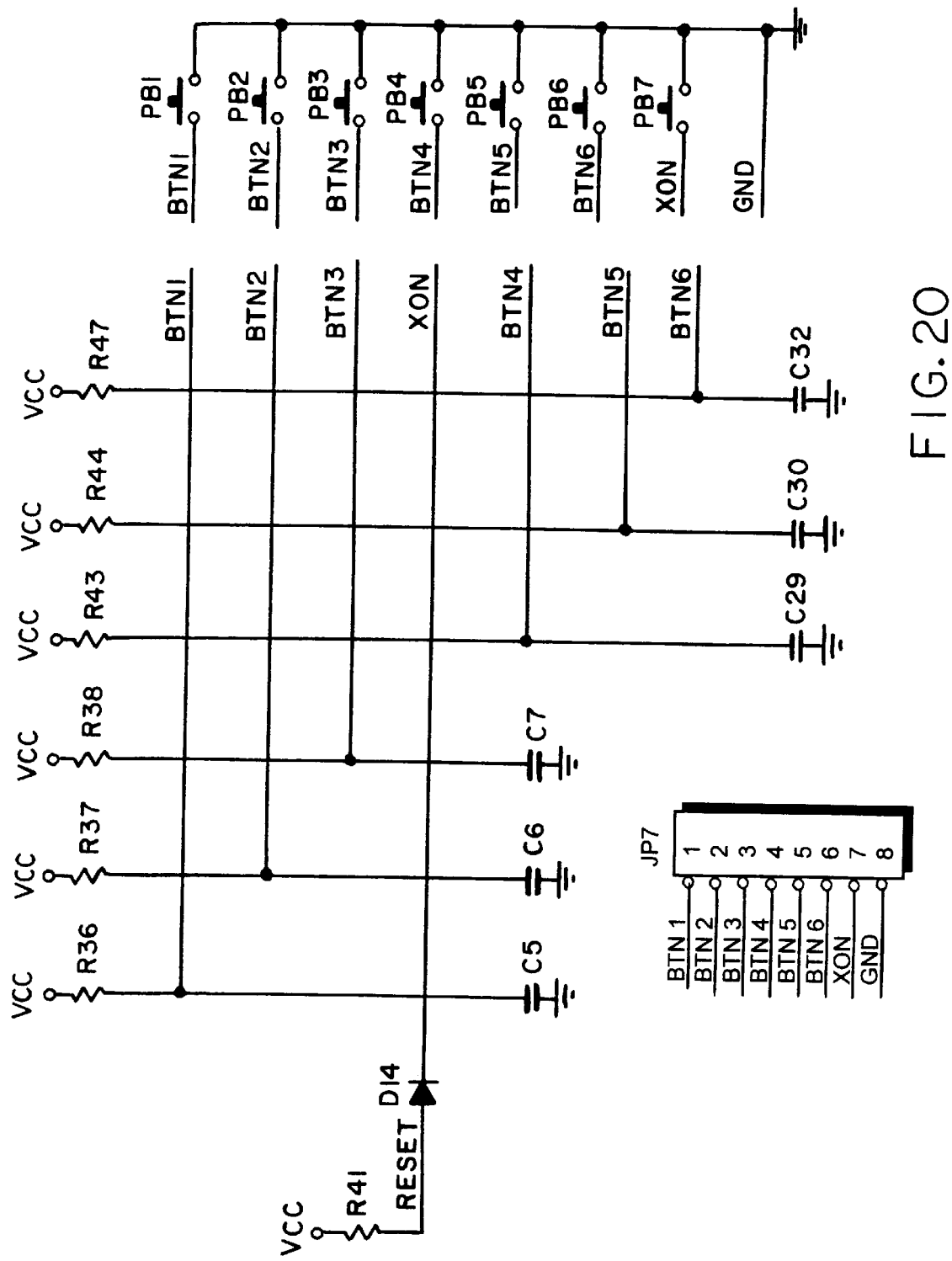
FIG. 20 illustrates a circuit that takes user input from the keyboard buttons and provides output to the liquid crystal display ("LCD") for a micro current device in accord with the present invention.

Waveform envelope is controlled by a MCU pulse width modulator "PWM" (see VPLMA, FIGS. 16A–16B) and the filter circuit illustrated in FIG. 16 (R45 and C31) feeding analog switches U2 (FIG. 26), which sets the maximum current output. This means that after a maximum current is selected (by the switches), it can be reduced as necessary to control the waveform by the microprocessor using its PWM output.

The MCU (U3) provides control of the H-Bridges (FIG. 22) through the circuitry illustrated in FIG. 16. FIG. 22 illustrates the output circuitry for one A and one B channel. The device of this embodiment basically has four channels for output current signals according to of each the A and B channels illustrated. All channels having an "A" output are the same and all channels having a "B" output are the same.

The polarity of the output current is controlled in the H-Bridge by reversing the output transistor connections with the analog switches U104 in the output circuit (FIG. 22). Output frequency is controlled by cycling these both switches on and off as the chosen frequency may require. Normally, one switch is on and the other is off for current flow.

All H-Bridge circuits as commanded produce the same current as selected by the user, e.g., between 40 and 180 micro amperes.

All side A channels are driven with the same signal and all B channels are driven by a different same signal. Thus, side A outputs produce different output frequency characteristics from side B outputs. Each channel can be individually programmed, if desired, so that each channel has different output frequency characteristics. Typically, in this embodiment, four channels (side A) have one output frequency characteristic and the other four channels (side B) have a second frequency characteristic.

In this embodiment, a speaker provides audible indications of current level flowing in the selected channel H-Bridge. The tone is produced by a voltage controlled oscillator U10,U11 (FIG. 18), which obtains its voltage control from a MCU PWM (see VPLMB, FIGS. 16A–16B) and filter (R88, C41). The tone can be varied over a wide range of audio frequencies. The volume is controlled by a set of analog switches and a latch U14,U12 (FIG. 18) in the primary side of the audio output transformer T3, which drives the speaker.

Figure 21:
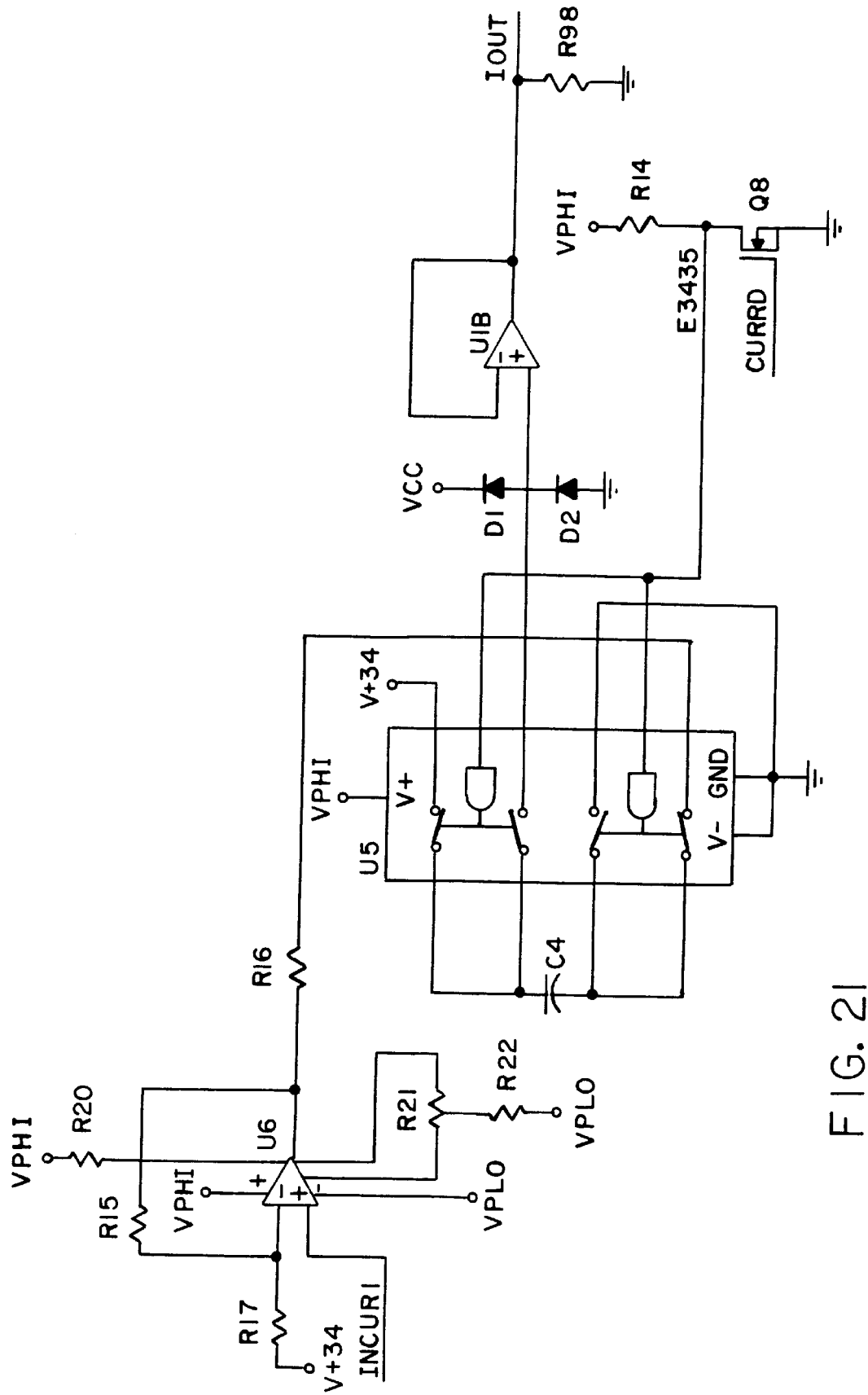
FIG. 21 illustrates an instrumentation circuit that amplifies signals and makes conversions for the LCD for the A side of the channel for a micro current device in accord with the present invention.

The MCU can obtain data from any signal channels "A" and "B" and display a current output representation of the output of any particular channel as selected by the user on the LCD. The data multiplexer ("Data Mux", FIG. 19) isolates and directs a single channel of data to the instrumentation unit. A control voltage level shifter (FIG. 17) provides the voltage conversion to control this analog multiplex circuit operation at high voltage. The single channel can be any of the eight channels as selected by the user. The instrumentation unit circuit amplifies the signal (see U6, FIG. 21) and converts the sensed signal from the H-Bridge high voltage to a low voltage that the MCU can read and from which it can calculate the necessary display. This is accomplished with a "flying capacitor" type voltage level convertor U5 (FIG. 21). The signal is then buffered (U1, FIG. 21) to feed the MCU an analog signal. The output current is depicted with a group of arrows on the LCD screen to illustrate relative output current level. Approximate current percentage is also displayed. A second such circuit is used for the B side channels.

In the circuits illustrated in FIGS. 16A–26, C__ designates a capacitor; D__ designates a diode (Schottky diodes (D3, D7), Zener diodes (D11, D12) or switching diodes can be used where appropriate); R__ designates a resistor (typically 0.25 watt); RT__ designates a temperature sensitive resistor; T__ designates a transformer; U2, U4, U11, U12, U104, U204 and U304 designate an analog CMOS switch; U14 and U21 designate a CMOS 4 bit latch; U6 and U16 designate a bi-fet op amp; U1, U7, U10, U107, U207 and U307 designate a CMOS low power op amp; U3 designates a central processor; U19 designates a dual quad analog switch; U17 designates a CMOS 555; U8 designates a quad 2in NOR gate CMOS; U5 and U15 designate a dual high voltage analog switch; U9 designates a power supply switching regulator; U18 designates an inverter; JP2 and JP5 designate a header to display LCD; JP6 designates a 3 pin female connector for back lights; JP7 designates pads for wire connect to buttons; JP3 designates connection to serial port; JP4, JP104, JP204 and JP304 designate an output header connector; PB__ designates a push button switch; L1 designates a low resistance choke; LS1 designates a small speaker; Q__ designates a transistor (MOSFET (Q8, Q10, Q20, Q21, Q22, Q23, Q24 and Q26), power MOSFET Q9 and Q18) or general purpose transistors where appropriate); and Y1 designates a 4 milli-Hz crystal.

In the embodiment illustrated, the time for a treatment session can be selected in stepped increments from 1 second to 120 minutes. The time displayed shows both the elapsed time as well as the time remaining on a particular program or time programmed on the LCD Screen.

The pulse width, or cycle time, can vary according to the patient treatment. For treatment for lymphedema using alternating negative and positive polarity pulses, it has been found advantageous to use a two second pulse followed by a one-half second pause.

For the 8 channel, micro current, interferential wave device described herein, the electrical output is applied to the patient through 16 conductive pads attached to the area of interest or through the cotton Q tips of dual channel probes. Four Q Tips of two dual channel probes can be connected in parallel to the same output as 4 of the pads. The unit can be used in combination with one probe used for one treatment of one part of the patient along with the 6 remaining channels used through pads, each pair of pads used for treatment in another part of the body. A diagram of the placement at the pads for treatment of the lymphatic system of the whole body is illustrated in FIG. 8A–8E. In the FIGS., each pair of pads is associated with a channel, a minus designating the negative pad and a plus designating the positive pad for applying a voltage and thus direct current to a body part or area.

At least two different frequencies are used by the 8 channel device. If two frequencies are used, four channels use one frequency while the remaining four channels use the second frequency. In the application illustrated by FIGS. 8A–8E, for example, channels 1, 3, 5 and 7 use the first frequency and channels 2, 4, 6 and 8 use the second frequency. However, as described above, each channel can have an independent frequency.

To begin a treatment procedure, the user presses the ON/RESET button (not shown) to power up the device. Various selection menus are displayed on the LCD display. The used may make selections by pressing the appropriate buttons. Once the desired parameters are selected, pressing the RUN button (not shown) will start the device, which will run until the selected time period is complete. The MCU sets the frequency and output based on user selections keeps track of the time, and stops when the desired time has been completed.

During the running of a wave form, the instrumentation circuitry measures the output current and output voltage. This data is returned to the MCU where, after calculations are completed, data is then displayed on the LCD's. Audio tones that are indicative tones of the levels of current flowing are present during the output of a wave form. Once the program time is completed, the unit returns to the selection menu. The unit will automatically shut itself off after six minutes, if no selection is made.

A typical treatment program of twenty sessions is illustrated in Table 1. Each session is divided into three portions of seven minutes each. The pads are located in the patient as shown in FIGS. 8A–8E. Frequency settings (Hz) for two frequencies, treatment time (min), wave form (gentle, mild) and electrical current ($\mu$A) are shown in the table. Note that the frequency is increased for each portion of a treatment session and between sessions, as illustrated. Also, the wave form is changed with later sessions. Alternating polarity between pulses is used, as described above.

The 16 pads can be positioned to concentrate treatment of the lymphatic system on the upper body by locating the pairs of pads as illustrated in FIGS. 9A–9D.

Figure 10A:
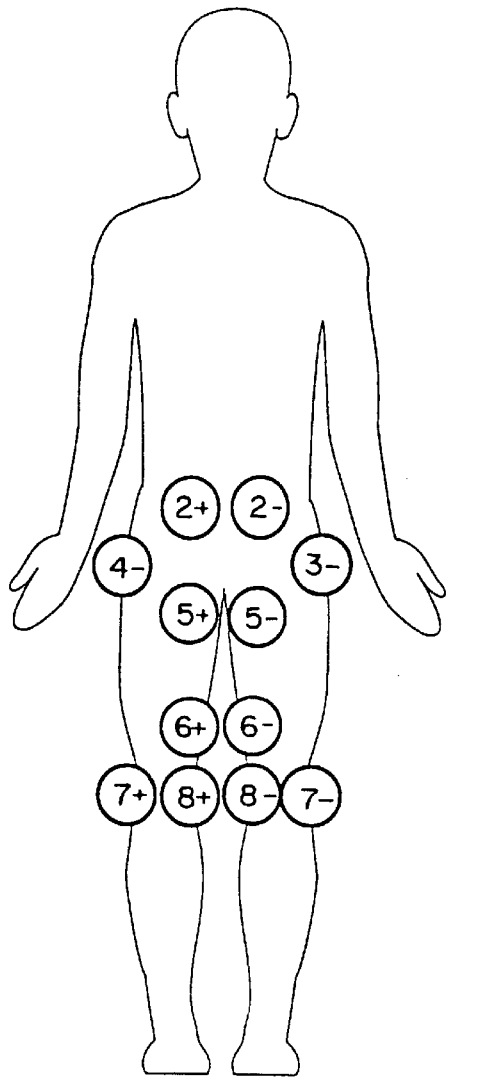
FIGS. 10A–10B illustrate the placement of pairs of conductive pads or electrodes for micro current treatment of a middle portion of the body in accord with certain embodiments of the present invention.
Figure 10B:
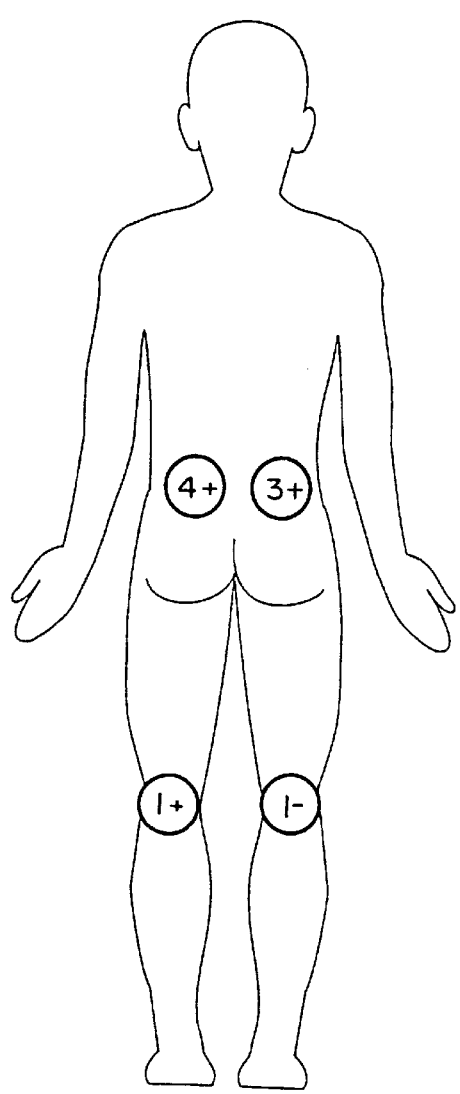

The 16 pads can be positioned to concentrate treatment of the lymphatic system on the upper body by locating the pairs of pads as illustrated in FIGS. 10A–10B.

Figure 11A:
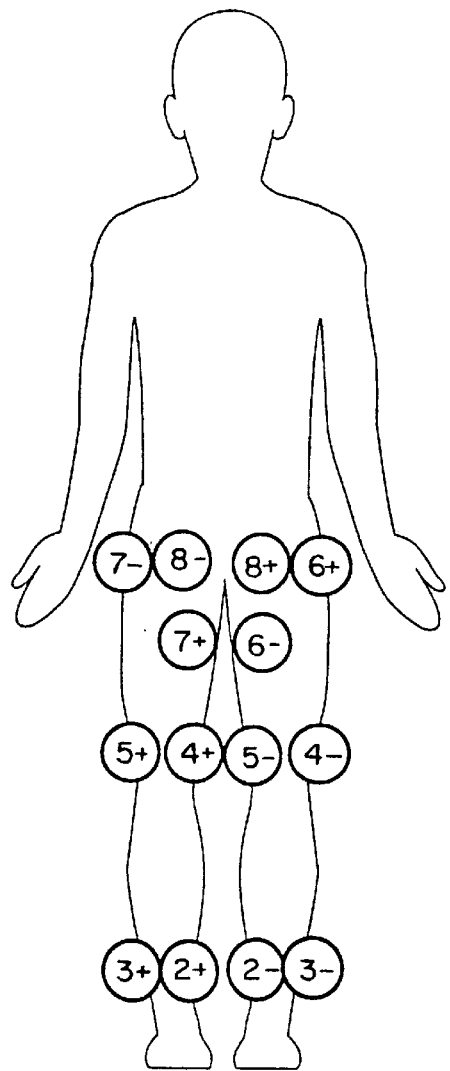
FIGS. 11A–11B illustrate the placement of pairs of conductive pads or electrodes for micro current treatment of the legs in accord with certain embodiments of the present invention.
Figure 11B:
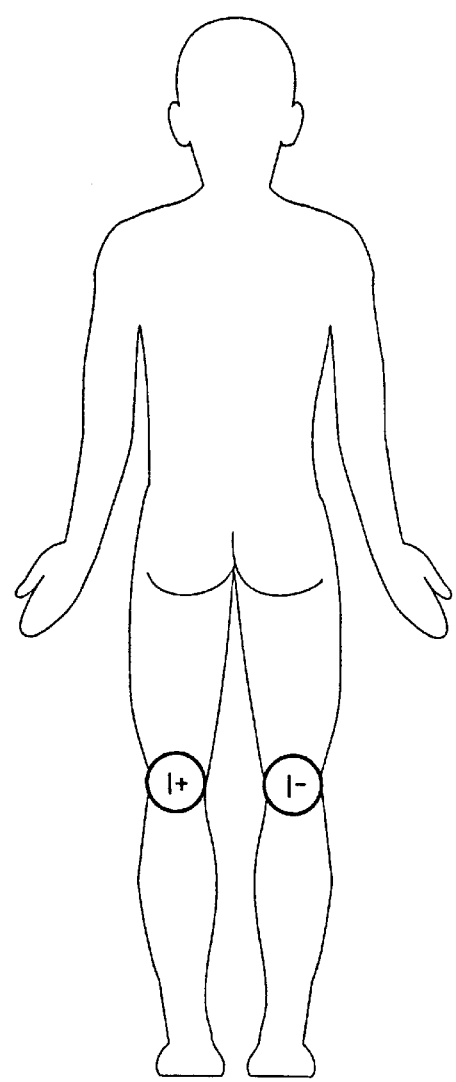

The 16 pads can be positioned to concentrate treatment of the lymphatic system on the upper body by locating the pairs of pads as illustrated in FIGS. 11A–11B.

Figure 12A:
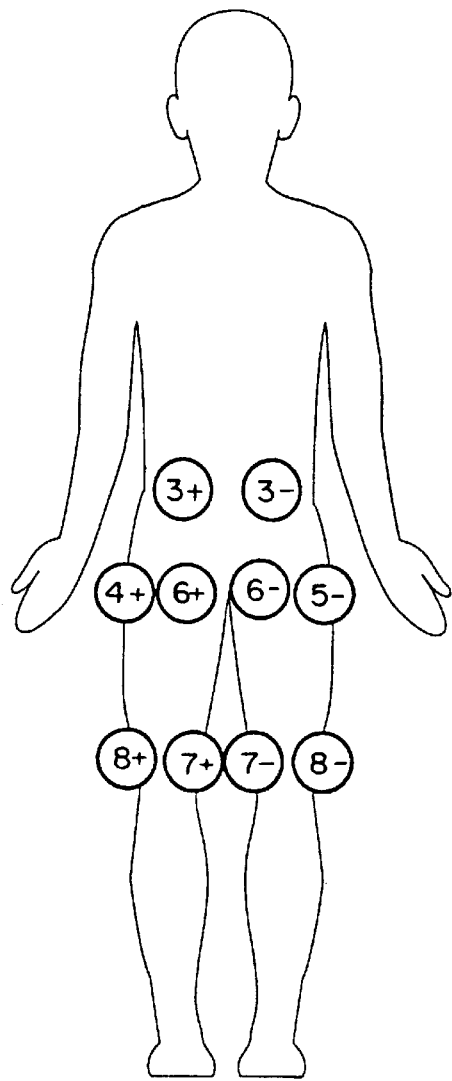
FIGS. 12A–12C illustrate the placement of pairs of conductive pads or electrodes for micro current treatment of a lower portion of the body in accord with certain embodiments of the present invention.
Figure 12B:
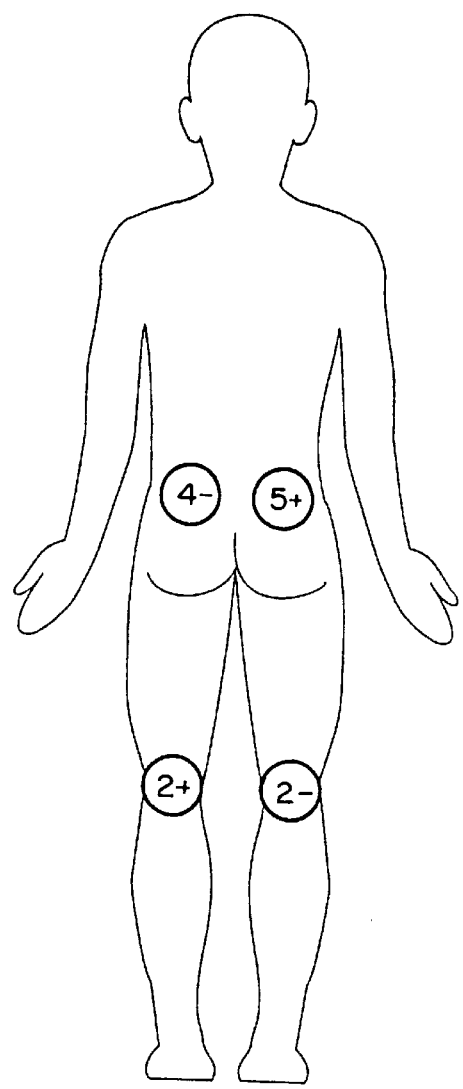
Figure 12C:
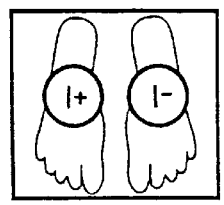

The 16 pads can be positioned to concentrate treatment of the lymphatic system on the upper body by locating the pairs of pads as illustrated in FIGS. 12A–12C.

Figure 13:
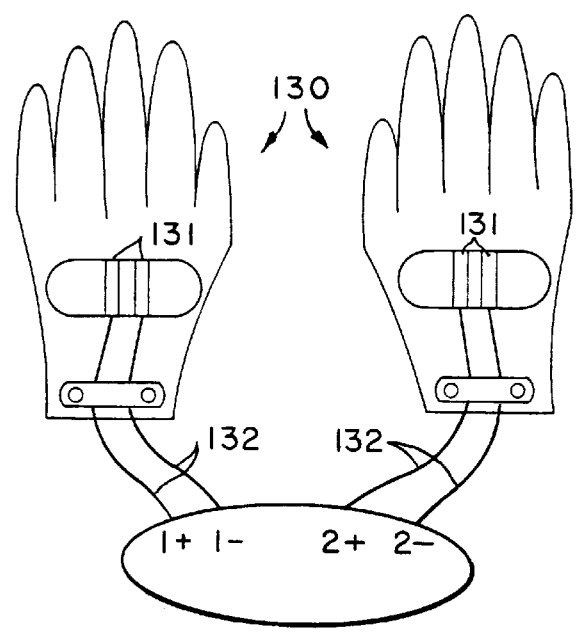
FIG. 13 illustrates a pair of gloves adapted and configured for use in connection with a micro current device of the present invention.
Figure 9A:
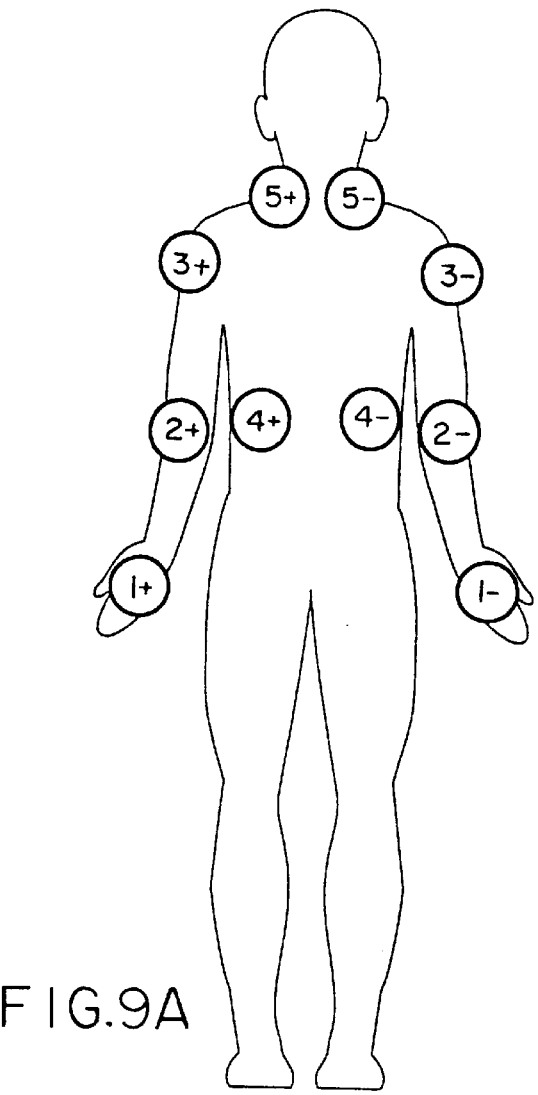
FIGS. 9A–9D illustrate the placement of pairs of conductive pads or electrodes for micro current treatment of the upper body in accord with certain embodiments of the present invention.
Figure 9B:
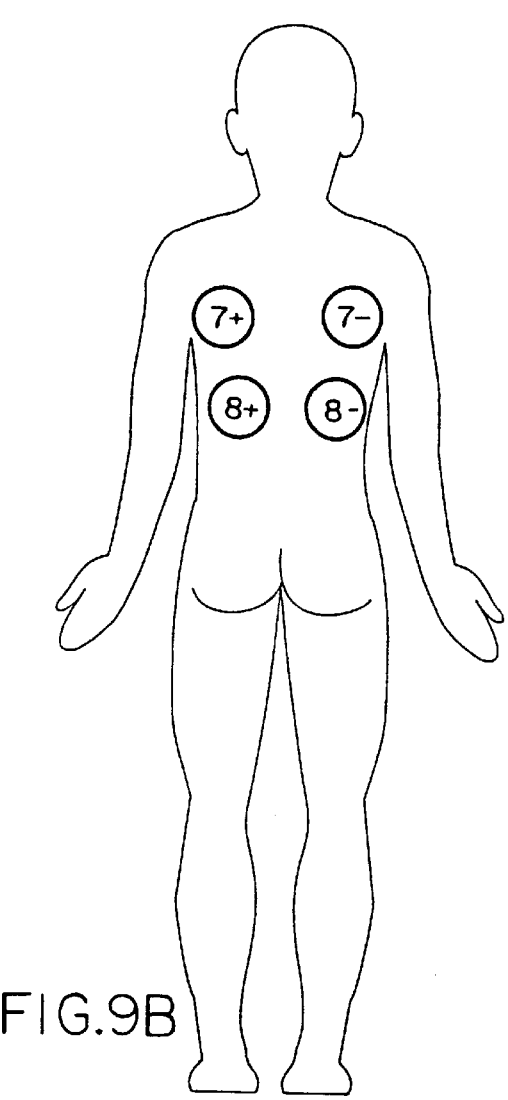
Figure 9C:
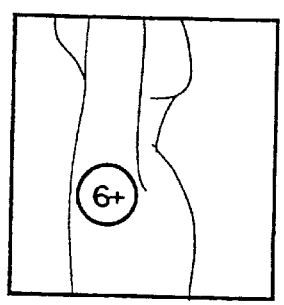
Figure 9D:
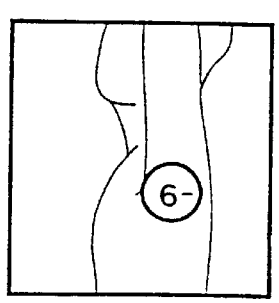

The pads can be used in combination with gloves in order to use the micro current treatment in combination with manual lymphatic drainage treatment. FIG. 13 illustrates are pair of gloves 130 adapted and configured for use with micro current, interferential wave treatment. Each glove has two conductive pads 131 located beneath the palm of the user. The pads are connected by electrical wires 132 to two or more channels of a micro current, interferential wave device.

The gloves are preferably made of a latex material. The conductive pads on the gloves are conveniently made of an acrylic copolymer containing about 5% by weight carbon black, about 0.1% by weight and about 0.1% by weight zinc. Any other conductive composition can be substituted.

The gloves can be connected to two channels of a micro current, interferential wave device, as illustrated in FIG. 13. The gloves are shown palms up. One glove is connected to the positive pole of each channel and the other glove is connected to the negative pole of each channel. Each channel uses a different frequency. When the gloves are placed in contact with the patient, current of the particular frequency modulation is conducted between corresponding pads completing the channel circuit. Thus, micro current and manual therapy can be combined.

The gloves can also be used in combination with pads to complete up to four channels circuits of the micro current, interferential wave device. For example, as illustrated in FIGS. 14A–14C, four pads can be positioned and electrically coupled to a pair of gloves for manual lymphatic drainage of the flank, upper leg, knee, posterior knee, ankle, foot and full leg in combination with micro current, interferential wave treatment. Manual movement of the gloves to massage the indicated body parts completes the micro current circuit during manual treatment.

Figure 15A:
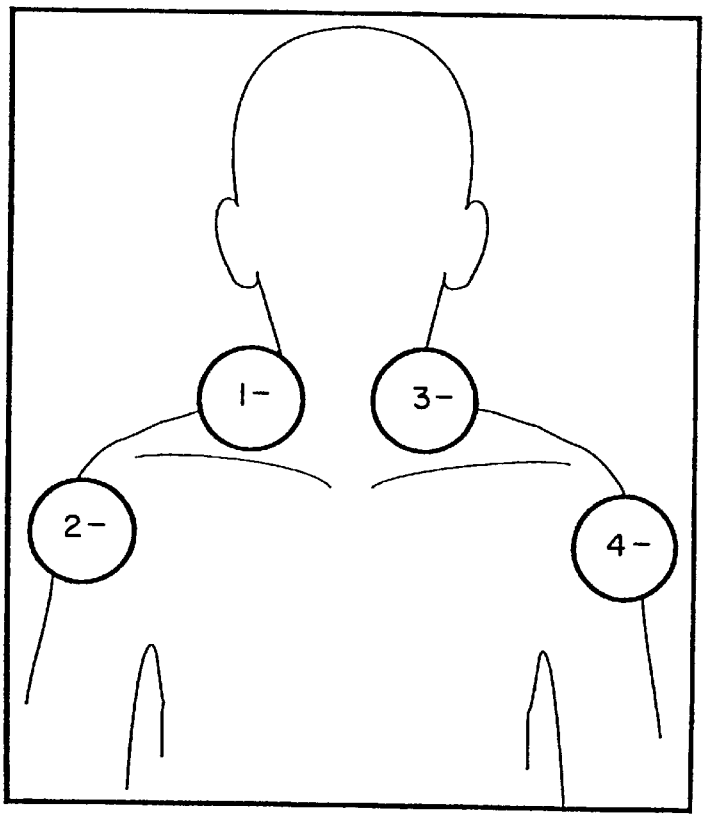
FIGS. 15A–15B illustrate the placement of conductive pads or electrodes for use in combination with the gloves of FIG. 13 for micro current treatment of a middle or upper portion of the body in accord with certain embodiments of the present invention.
Figure 15B:
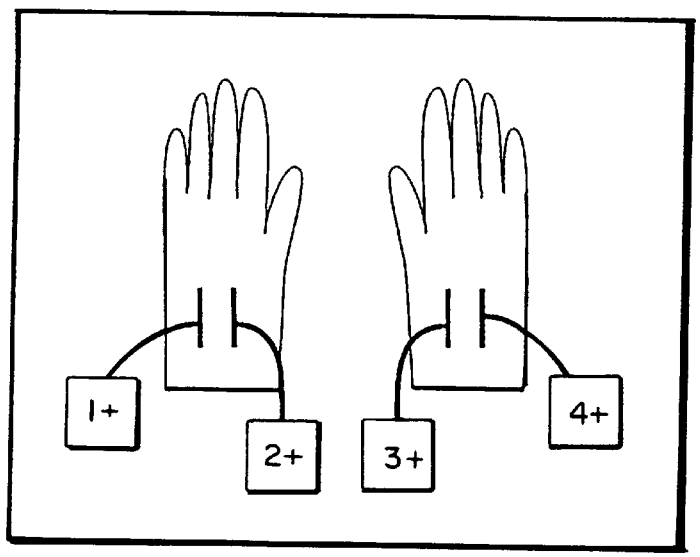

Positioning of four pads as illustrated in FIG. 15A–15B in combination with the gloves can provide manual lymphatic drainage of the arms, stomach and back in combination with micro current, interferential wave treatment.

By positioning the pads as illustrated in FIG. 15A and using the gloves to massage the face, head and neck, manual lymphatic drainage of those portions of the body also can be combined with micro current, interferential wave treatment.

Treatment sessions similar to those illustrated in Table 1, i.e., segmented into three portions with increased frequency and wave form are preferred.

In a study of 65 patients exhibiting lymphedema and/or fibrosis treated with a micro current device in accord with the present invention, all patients showed moderate to dramatic response to the micro current treatment.

The invention has been described in detail with reference to preferred embodiments thereof. However, it will be appreciated that, upon consideration of the present specification and drawings, those skilled in the art may make modifications and improvements within the spirit and scope of this invention as defined by the claims.

TABLE 1

TREATMENT PROGRAM

| TREATMENT SESSION NO. | FREQUENCY 1 (Hz) | TIME (min) | WAVE FORM | CURRENT ($\mu$A) | FREQUENCY 2 (Hz) |
|---|---|---|---|---|---|
| 1,2 | 0.05 | 7 | Gentle | 40 | 0.07 |
|  | 10 | 7 | Gentle | 40 | 11 |
|  | 150 | 7 | Gentle | 40 | 300 |
| 3,4 | 0.07 | 7 | Gentle | 40 | 0.09 |
|  | 11 | 7 | Gentle | 40 | 12 |
|  | 150 | 7 | Gentle | 40 | 300 |
| 5,6 | 0.09 | 7 | Gentle | 40 | 1.1 |
|  | 9 | 7 | Gentle | 40 | 10 |
|  | 150 | 7 | Gentle | 40 | 300 |
| 7,8 | 1.1 | 7 | Gentle | 40 | 1.5 |
|  | 12 | 7 | Gentle | 40 | 13 |
|  | 150 | 7 | Gentle | 40 | 300 |
| 9,10 | 1.5 | 7 | Gentle | 40 | 2 |
|  | 10 | 7 | Gentle | 40 | 11 |
|  | 150 | 7 | Gentle | 40 | 300 |
| 11,12 | 0.5 | 7 | Mild | 40 | 0.07 |
|  | 11 | 7 | Mild | 40 | 12 |
|  | 150 | 7 | Mild | 40 | 300 |
| 13,14 | 0.07 | 7 | Mild | 40 | 0.09 |
|  | 9 | 7 | Mild | 40 | 10 |
|  | 150 | 7 | Mild | 40 | 300 |
| 15,16 | 0.09 | 7 | Mild | 40 | 1.1 |
|  | 11 | 7 | Mild | 40 | 12 |
|  | 150 | 7 | Mild | 40 | 300 |
| 17,18 | 1.1 | 7 | Mild | 40 | 1.5 |
|  | 10 | 7 | Mild | 40 | 11 |

TABLE 1-continued

TREATMENT PROGRAM

| TREATMENT SESSION NO. | FREQUENCY 1 (Hz) | TIME (min) | WAVE FORM | CURRENT (µA) | FREQUENCY 2 (Hz) |
|---|---|---|---|---|---|
|  | 150 | 7 | Mild | 40 | 300 |
| 19,20 | 1.5 | 7 | Mild | 40 | 2 |
|  | 12 | 7 | Mild | 40 | 13 |
|  | 150 | 7 | Mild | 40 | 300 |

I claim:

1. An interferential wave, micro current device, said device comprising:
   a power supply;
   a frequency generator;
   a pulse generator;
   a pulse envelope generator;
   an electrical current controller; and
   four or more channels for applying micro amperes of electrical current to patient tissue, each channel having two electrodes for completing a micro current electrical circuit through patient tissue;
   wherein the controller provides a controlled amount of current in each channel from about 20 micro amperes to about 200 micro amperes at a frequency up to about 300 Hertz.

2. The interferential wave, micro current device in accord with claim 1, wherein the controller provides pulsed energy waveform envelopes of micro current with a pause after each pulse envelope.

3. The interferential wave, micro current device in accord with claim 2, wherein the pause after each pulse envelope is from about 10% to about 25% of the length of the pulse envelope.

4. The interferential wave, micro current device in accord with claim 2, wherein the pause is about 0.5 second.

5. The interferential wave, micro current device in accord with claim 1, wherein the controller provides pulsed energy waveform envelopes of micro current that are modulated by a fifty percent duty cycle square wave.

6. The interferential wave, micro current device in accord with claim 1, wherein the controller provides a first pulsed energy waveform envelopes having a first frequency to at least one channel and a second pulsed energy waveform envelopes having a second frequency to at least one other channel to provide an interferential wave form.

7. The interferential wave, micro current device in accord with claim 1, further comprising a central processing unit to control the generation the pulse, the pulse envelope, the frequency in each channel, and the amount of electrical current in each channel.

8. The interferential wave, micro current device in accord with claim 1, wherein the device has eight channels.

9. The interferential wave, micro current device in accord with claim 1, wherein the controller provides pulsed energy waveform envelopes of micro current and wherein the pulses alternate in polarity.

10. The interferential wave, micro current device in accord with claim 9, wherein initial pulse is negative in charge.

11. The interferential wave, micro current device in accord with claim 1, wherein the controller provides pulsed energy waveform envelopes of micro current and wherein the waveform envelope has a leading edge wherein the current changes from zero to its maximum or minimum value in from about 1 milliseconds to about 500 milliseconds.

12. The interferential wave, micro current device in accord with claim 1, wherein the controller provides pulsed energy waveform envelopes of micro current and wherein the waveform envelope has a leading edge wherein the current changes from zero to its maximum or minimum value in from about 100 milliseconds to about 500 milliseconds.

13. The interferential wave, micro current device in accord with claim 1, wherein the controller provides pulsed energy waveform envelopes of micro current and wherein the waveform envelope has a trailing edge wherein the current changes from its maximum or minimum value to zero in from about 1 milliseconds to about 500 milliseconds.

14. The interferential wave, micro current device in accord with claim 1, wherein the controller provides pulsed energy waveform envelopes of micro current and wherein the waveform envelope has a trailing edge wherein the current changes from its maximum or minimum value to zero in from about 100 milliseconds to about 500 milliseconds.

15. The interferential wave, micro current device in accord with claim 1, wherein the controller provides pulsed energy waveform envelopes of micro current and wherein the waveform envelope has a leading edge and a trailing edge wherein the current changes from zero to its maximum or minimum value, or from its maximum or minimum value to zero, in from about 1 milliseconds to about 500 milliseconds.

16. The interferential wave, micro current device in accord with claim 1, wherein the controller provides pulsed energy waveform envelopes of micro current and wherein the waveform envelope has a leading edge and a trailing edge wherein the current changes from zero to its maximum or minimum value, or from its maximum or minimum value to zero, in from about 100 milliseconds to about 500 milliseconds.

17. The interferential wave, micro current device in accord with claim 1, wherein the controller provides pulsed energy waveform envelopes of micro current in one of a plurality of waveform envelopes as selected by the user.

18. A method for treating a patient having lymphedema to improve lymphatic flow, said method comprising:
   providing multiple pairs of electrodes, each pair of electrodes connected to an electrical source defining a channel to provide a micro current of electricity across patient tissue;
   positioning about four or more pairs of electrodes on the patient each electrode being positioned proximal to a center of lymph nodes;
   providing a controlled current from about 20 µA to about 200 µA in each channel at a frequency of up to 300 Hz;
   providing a first frequency to at least one channel and a second frequency to at least one other channel to provide an interferential wave form; and
   providing pulsed energy to the patient using a wave form envelope with a mandatory pause between pulses.

19. The method for treating a patient having lymphedema to improve lymphatic flow in accord with claim 18, the method further comprising providing pulsed energy waveform envelopes of micro current that are modulated by a fifty percent duty cycle square wave.

20. The method for treating a patient having lymphedema to improve lymphatic flow in accord with claim 18, the method further comprising providing pulsed energy waveform envelopes having a first frequency to at least one channel and a second pulsed energy waveform envelopes having a second frequency to at least one other channel to provide an interferential wave form.

21. The method for treating a patient having lymphedema to improve lymphatic flow in accord with claim 18, the method further comprising providing eight channels.

22. The method for treating a patient having lymphedema to improve lymphatic flow in accord with claim 18, the method further comprising providing pulsed energy waveform envelopes of micro current wherein the pulses alternate in polarity.

23. The method for treating a patient having lymphedema to improve lymphatic flow in accord with claim 22, wherein initial pulse is negative in charge.

24. The method for treating a patient having lymphedema to improve lymphatic flow in accord with claim 18, the method further comprising providing pulsed energy waveform envelopes of micro current wherein the waveform envelope has a leading edge wherein the current changes from zero to its maximum or minimum value in from about 1 milliseconds to about 500 milliseconds.

25. The method for treating a patient having lymphedema to improve lymphatic flow in accord with claim 18, the method further comprising providing pulsed energy waveform envelopes of micro current wherein the waveform envelope has a trailing edge wherein the current changes from its maximum or minimum value to zero in from about 1 milliseconds to about 500 milliseconds.

26. The method for treating a patient having lymphedema to improve lymphatic flow in accord with claim 18, the method further comprising providing pulsed energy waveform envelopes of micro current wherein the waveform envelope has a leading edge and a trailing edge wherein the current changes from zero to its maximum or minimum value, or from its maximum or minimum value to zero, in from about 1 milliseconds to about 500 milliseconds.

27. The method for treating a patient having lymphedema to improve lymphatic flow in accord with claim 18, the method further comprising providing a pair of gloves having conductive pads located in a palm portion of each glove, the conductive pads being connected to two or more channels, and massaging the patient while current is conducted through the pads.

28. A method for treating a patient having edema to reduce swelling, said method comprising:
   providing multiple pairs of electrodes, each pair of electrodes connected to an electrical source defining a channel to provide a micro current of electricity across patient tissue;
   positioning about four or more pairs of electrodes on the patient each pair of electrodes being separated by an area of tissue suffering from edema;
   providing a controlled current from about 20 $\mu$A to about 200 $\mu$A in each channel at a frequency of up to 300 Hz;
   providing a first frequency to at least one channel and a second frequency to at least one other channel to provide an interferential wave form; and
   providing pulsed energy to the patient using a wave form envelope with a mandatory pause between pulses.

29. A method for treating a patient having fibrosis to reduce the occurrence thereof, said method comprising:
   providing multiple pairs of electrodes, each pair of electrodes connected to an electrical source defining a channel to provide a micro current of electricity across patient tissue;
   positioning about four or more pairs of electrodes on the patient each pair of electrodes being separated by an area of tissue suffering from fibrosis;
   providing a controlled current from about 20 $\mu$A to about 200 $\mu$A in each channel at a frequency of up to 300 Hz;
   providing a first frequency to at least one channel and a second frequency to at least one other channel to provide an interferential wave form; and
   providing pulsed energy to the patient using a wave form envelope with a mandatory pause between pulses.

30. A method for treating a patient having fibromylagea to reduce the occurrence thereof, said method comprising:
   providing multiple pairs of electrodes, each pair of electrodes connected to an electrical source defining a channel to provide a micro current of electricity across patient tissue;
   positioning about four or more pairs of electrodes on the patient each pair of electrodes being separated by an area of tissue suffering from fibromylagea;
   providing a controlled current from about 20 $\mu$A to about 200 $\mu$A in each channel at a frequency of up to 300 Hz;
   providing a first frequency to at least one channel and a second frequency to at least one other channel to provide an interferential wave form; and
   providing pulsed energy to the patient using a wave form envelope with a mandatory pause between pulses.

* * * * *